(12) United States Patent
Xavier Da Silveira et al.

(10) Patent No.: US 10,595,777 B2
(45) Date of Patent: Mar. 24, 2020

(54) METHOD AND DEVICE FOR HYDRATION MONITORING

(71) Applicant: PERFORMANCE ATHLYTICS, Austin, TX (US)

(72) Inventors: Paulo E. Xavier Da Silveira, Boulder, CO (US); Joseph Schmitt, Andover, MA (US); Byron Olson, Boone, IA (US); Nithin O. Rajan, Austin, TX (US); Dustin M. Freckleton, Austin, TX (US); David E. Clift-Reaves, Austin, TX (US)

(73) Assignee: LVL TECHNOLOGIES, INC., Austin, TX (US)

( * ) Notice: Subject to any disclaimer, the term of this patent is extended or adjusted under 35 U.S.C. 154(b) by 452 days.

(21) Appl. No.: 15/588,508

(22) Filed: May 5, 2017

(65) Prior Publication Data

US 2017/0319131 A1   Nov. 9, 2017

Related U.S. Application Data

(60) Provisional application No. 62/333,011, filed on May 6, 2016.

(51) Int. Cl.
*A61B 5/00* (2006.01)
*A61B 5/0295* (2006.01)
(Continued)

(52) U.S. Cl.
CPC .......... *A61B 5/4875* (2013.01); *A61B 5/1455* (2013.01); *A61B 5/14546* (2013.01); *A61B 5/443* (2013.01); *A61F 13/42* (2013.01); *A61F 13/84* (2013.01); *G01N 21/3554* (2013.01); *A61B 5/14542* (2013.01); *A61B 5/6824* (2013.01); *A61B 2562/043* (2013.01); *G01N 21/359* (2013.01); *G01N 21/49* (2013.01); *G01N 33/49* (2013.01)

(58) Field of Classification Search
CPC ... A61B 5/0059; A61B 5/0064; A61B 5/1455; A61B 5/14546; A61B 5/443; A61B 5/4875; A61B 5/6833; A61B 5/72; A61B 5/7271; G01N 21/3554
See application file for complete search history.

(56) References Cited

U.S. PATENT DOCUMENTS 6,442,408 B1 * 8/2002 Wenzel .............. A61B 5/14532
 600/310
7,657,292 B2 * 2/2010 Baker, Jr. ............. A61B 5/0059
 600/310

* cited by examiner

*Primary Examiner* — Eric F Winakur
(74) *Attorney, Agent, or Firm* — Polsinelli PC

(57) ABSTRACT

Provided herein are methods and devices operable to monitor the hydration of a user. The wearable device for hydration monitoring includes an emitting component operable to emit light having at least three different wavelengths, a sensor operable to receive a reflected portion of the emitted light, and a processor operable to receive signals from the sensor. At least one of the wavelengths is in the range from 900 nm to 1600 nm for optical detection of a level of water. The method for hydration monitoring includes emitting light from a light emitting component operable to emit light having at least three different wavelengths and detecting light with at least one photodetector. At least three distances between the light emitting component and the photodetector are known and the at least three distances allow monitoring of at least two different tissue beds with at least two different tissue depths.

19 Claims, 30 Drawing Sheets

(51) Int. Cl.
*A61B 5/145* (2006.01)
*A61B 5/026* (2006.01)
*A61F 13/537* (2006.01)
*G01N 21/3554* (2014.01)
*A61B 5/1455* (2006.01)
*A61F 13/84* (2006.01)
*A61F 13/42* (2006.01)
*G01N 33/49* (2006.01)
*G01N 21/359* (2014.01)
*G01N 21/49* (2006.01)

METHOD AND DEVICE FOR HYDRATION MONITORING

CROSS REFERENCE TO RELATED APPLICATIONS

This application claims priority to U.S. Provisional Application No. 62/333,011, filed May 6, 2016, the contents of which are entirely incorporated by reference herein.

FIELD

The present disclosure generally relates to a method and device for non-invasive tissue monitoring. More particularly, the disclosure relates to an apparatus and method for real-time assessment of bodily hydration using optical techniques.

BACKGROUND

Hydration is important for both physical and mental performance. Non-invasive methods for measuring hydration include weighing oneself before and after exercise to determine the amount of water lost in perspiration. Additionally, hydration is also measured based on the production of urine, which can be combined with the weight loss to determine total water loss.

BRIEF DESCRIPTION OF THE DRAWINGS

So that the manner in which the above recited features of the present disclosure can be understood in detail, a more particular description of the present disclosure, may be had by reference to embodiments, some of which are illustrated in the appended drawings. It is to be noted, however, that the appended drawings illustrate only typical examples, and are therefore not to be considered limiting of its scope, for the disclosure may admit to other equally effective embodiments.

DETAILED DESCRIPTION

Figure 1:
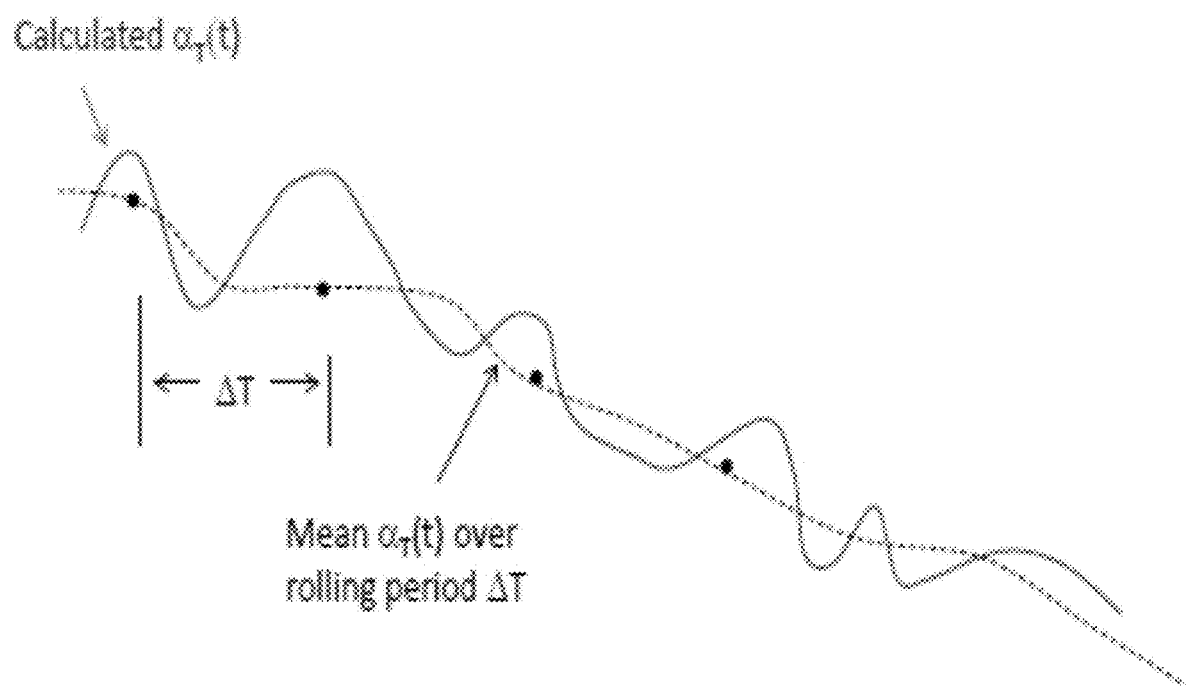
FIG. 1 is a plot illustrating an adaptive method for improved hydration detection in the presence of blood volume variations.

Various embodiments of the disclosure are discussed in detail below. While specific implementations are discussed, it should be understood that this is done for illustration purposes only. A person skilled in the relevant art will understand that other components and configurations can be used without parting from the spirit and scope of the disclosure.

It should be understood at the outset that although illustrative implementations of one or more embodiments are illustrated below, the disclosed device can be implemented using any number of techniques. The disclosure should in no way be limited to the illustrative implementations, drawings, and techniques illustrated herein, but can be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and can also include indirect interaction between the elements described. In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of the present disclosure upon reading the following detailed description, and by referring to the accompanying drawings.

The present disclosure generally relates to a method and device for tissue hydration monitoring. In one example, a method for tissue hydration monitoring is disclosed. The method involves emitting light from a light emitting component that emits light having at least three different wavelengths and detecting the light reflected from the least three different wavelengths. At least one of the wavelengths is in the range from 900 nm to 1600 nm for optical detection of a level of water. In another example, the method involves capturing light reflected from at least three different wavelengths, at least one of them in the range from 900 nm to 1200 nm for optical detection of a level of water. The later range can provide some added benefit through the ability to reduce costs and allow for expanded functionality. In one example, two of the three different wavelengths can have peak wavelengths of approximately the range between 920 nm and 1030 nm.

The method can further include detecting a slowly-varying analyte, where the slowly varying analyte is one or more of collagen, lipid, cytochrome oxidase, melanin, or total hemoglobin. In an example, the method can include detecting at least one of a level of collagen and a level of lipid. This example can further include calculating a ratio between the level of water and at least one of the level of collagen or lipid.

The method can further involve detecting the light with at least one photodetector, wherein at least three distances between the light emitting component and the photodetector are known, and the at least three distances allow monitoring of at least two different tissue beds with at least two different tissue depths. In an example, the at least three distances are 8 mm, 14 mm, and 22 mm. One tissue bed can be a shallow tissue bed and another tissue bed can be a deep tissue bed. For example, the shallow tissue bed is a lipid and the deep tissue bed is a muscle, or the shallow tissue bed is an epidermis and the deep tissue bed is a lipid or a muscle, or the shallow tissue bed is one of an epidermis or bone and the deep tissue bed is one of a subarachnoid space, a cerebral spinal fluid, or gray matter. The method can further include calculating the ratio of signals from the different tissue beds. The ratio of signals from different tissue beds can be used to detect water migration between different tissue beds or differentiate between posture and hydration changes. In an example, one of the at least two different tissue depths is used as a reference. The depth used as a reference can be optimized for a given user to adapt to a difference in tissue thickness and it can be derived from an interpolation of the other depths.

The method can further include using a cross-correlation, a non-linear regression, or a weighted sum of hydration and other terms to cancel out at least one other physiological change. The at least one physiological change can include at least one of blood volume, oxygenation, motion, or pressure change.

The method can further involve calculating a regression to determine at least one of a blood volume level and/or a hydration level. The regression can be a linear regression or a non-linear regression.

The method further involves calculating a vector projection selected for hydration monitoring. The present disclosure includes hydration monitoring that can include the removal of noise from changes in blood volume, total hemoglobin content, and other sources of noise. Removal of noise is through a vector projection capable of minimizing noise and selected in order to deliver the most accurate, real-time hydration information possible.

In another example, the method for tissue hydration monitoring can include adapting a weighting of the wavelengths to remove interference. The interference can vary over a time interval substantially shorter than that of the slowly varying analyte. The weightings of the wavelengths for prediction of tissue water content are fixed values determined from calibration experiments performed on a group of individuals. Therefore, they represent average values of optical properties of a group of individuals over time. The optical path lengths and tissue geometry varies from subject to subject, as well as in one subject over time.

Based on the results of experiments, it appears that imperfect subtraction of the variations of the total hemoglobin content ($Hb_T$) may be a major source of noise/error in the hydration measurements. A possible solution to this problem is to assume that $H_2O$, collagen, and lipid content remain constant over a much longer time period than $Hb_T$. The variance of the total measured attenuation can be minimized over the long fixed time intervals by adding a continuously adjustable error term to the weightings of the optical densities that contribute to the $Hb_T$ estimate. This process is illustrated by FIG. 1. Alternatively, the blood volume interference to the hydration signal may be estimated by the cross-correlation between the hemoglobin signal and the hydration signal and the interference may be cancelled out by subtracting the hemoglobin signal from the hydration signal after multiplication by the cross-correlation coefficient.

Since the standard multiple regression approach has limited efficacy to reduce the effects of blood volume variations enough to allow accurate estimate of tissue hydration, supplemental methods are needed to further attenuate these effects. One possible approach is to estimate blood volume in the tissue using multiple-wavelength regression and then use the estimated blood volume to adjust the regression coefficients of the water regression equation.

In this approach, the coefficients of the water estimation equation become a function of percent blood volume ($V_b$). For the 4-λ, case:

$$W = b_0(V_b) + b_1(V_b)OD_{\lambda 1} + b_2(V_b)OD_{\lambda 2} + b_3(V_b)OD_{\lambda 3} + b_4(V_b)OD_{\lambda 4}$$

Figure 2:
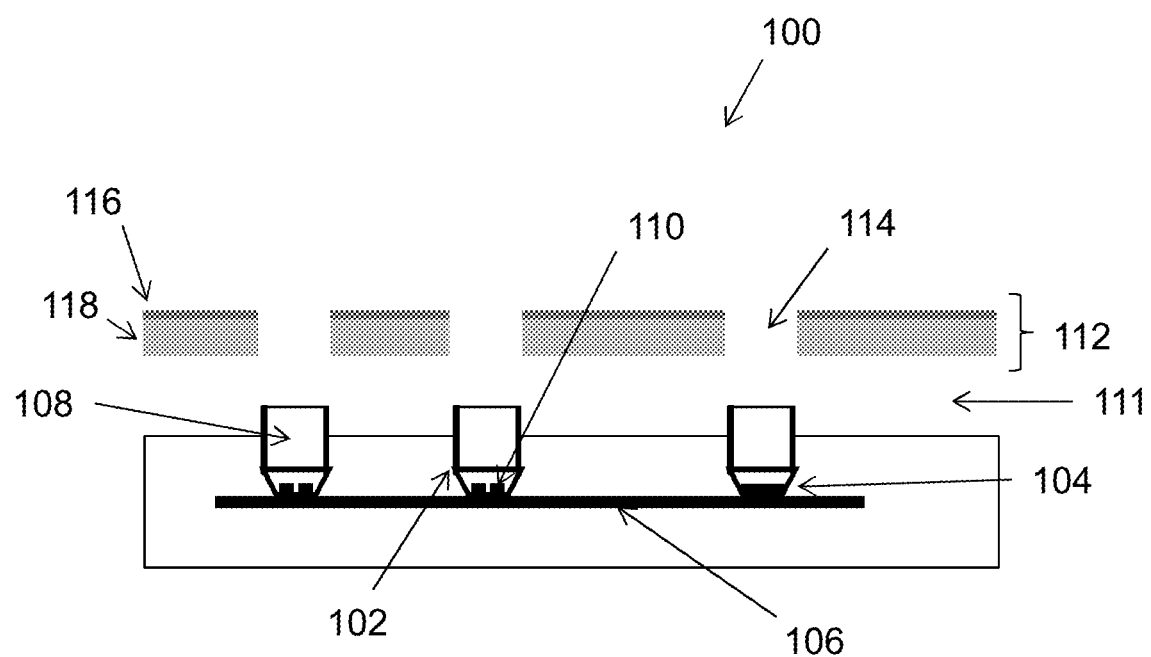
FIG. 2 is a depiction of a moisture wicking design of the device according to the present disclosure.

In another example, a wearable device for hydration monitoring is disclosed. FIG. 2 is a depiction of a multilayered device according to a possible embodiment of the present disclosure. The wearable device can include an emitting component operable to emit light having at least three different wavelengths, a sensor operable to receive a reflected portion of the emitted light, and a processor operable to receive signals from the sensor. The device can further include a recessed cavity to avoid excess pressure, at least one breathing channel to aerate a space between the sensor and the skin, wherein the breathing channel comprises at least one of a capillary tube, an air channel with optical baffling, and micro-holes, and a layered material between the skin and the sensor capable of wicking moisture away from the sensor. In an example, the layered material can have a first layer comprising a breathable polymer and a second layer comprising a wicking material. In another example, the layered material comprises a first layer comprising an adhesive, a second layer comprising a wicking material, and a third layer comprising a water-absorbing material.

In various examples, the processor can be operable to receive signals from the sensor and to calculate a vector projection selected for hydration monitoring or to calculate a regression to determine at least one of a blood volume level and/or a hydration level. In an example, the sensor is a photodetector operable to receive a reflected portion of the emitted light. In this example, at least three distances between the light emitting component and the photodetector are known, and the at least three distances allow monitoring of at least two different tissue beds with at least two different tissue depths. The at least three distances can be 8 mm, 14 mm, and 22 mm. The device can be further operable to control pressure to regulate a hydration level of the skin underneath the sensor.

Figure 3:
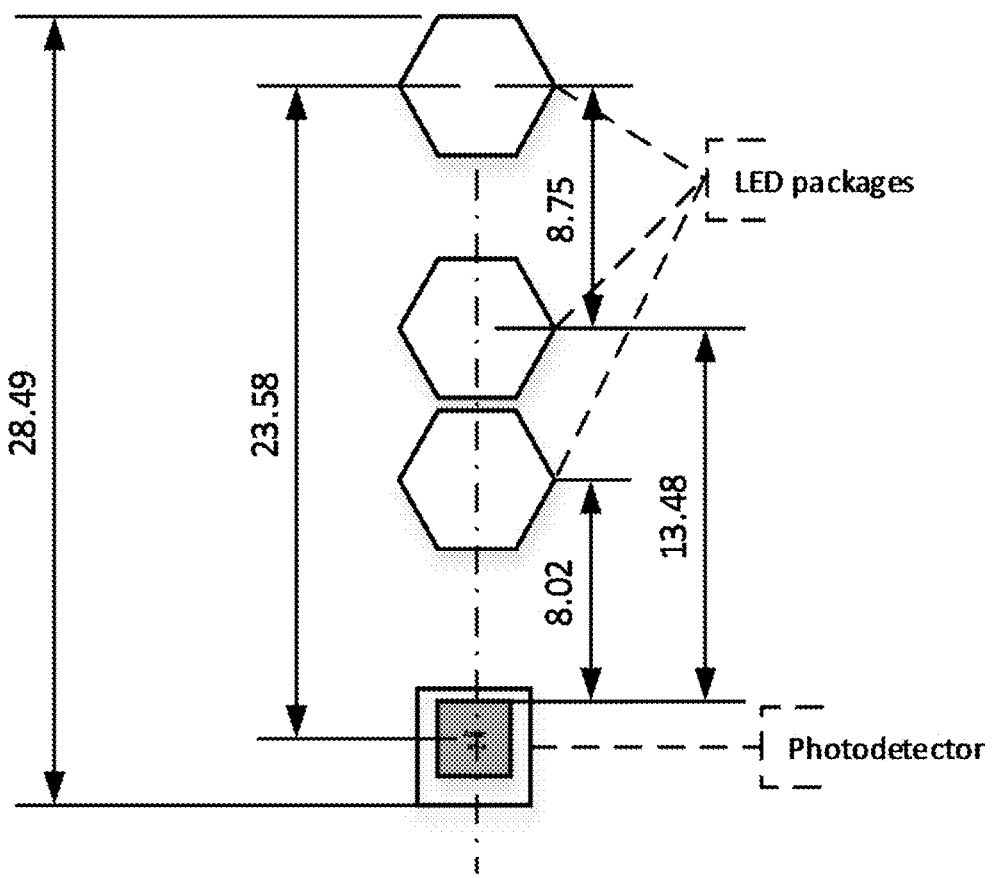
FIG. 3 is a depiction of the arrangement of LEDs and photodiodes according to an example of the present disclosure.

FIG. 3 is a depiction of the arrangement of LEDs and photodiodes according to an example of the present disclosure. The spacing between the LED and the photodiode affects the depth of tissue that the emitted light will penetrate, and thus having different spacings between the LEDs and the photodiode enables the hydration monitoring of different tissue beds. For example, an approximate eight millimeter spacing and approximate fourteen millimeter spacing between the LED and the photodiode enables monitoring of the hydration of the dermis and epidermis, whereas an approximate spacing of fourteen millimeters and approximate twenty-two millimeter spacing enables monitoring of the hydration of the muscle when the sensor is placed over a large skeletal muscle. For example, the brachioradialis or the gastrocnemius muscles. Note that the position of illuminators (LEDs) and photodiodes can be exchanged to the same effect. That is, functionally equivalent signals can be generated by replacing all LEDs with photodetectors and vice versa.

Figure 4:
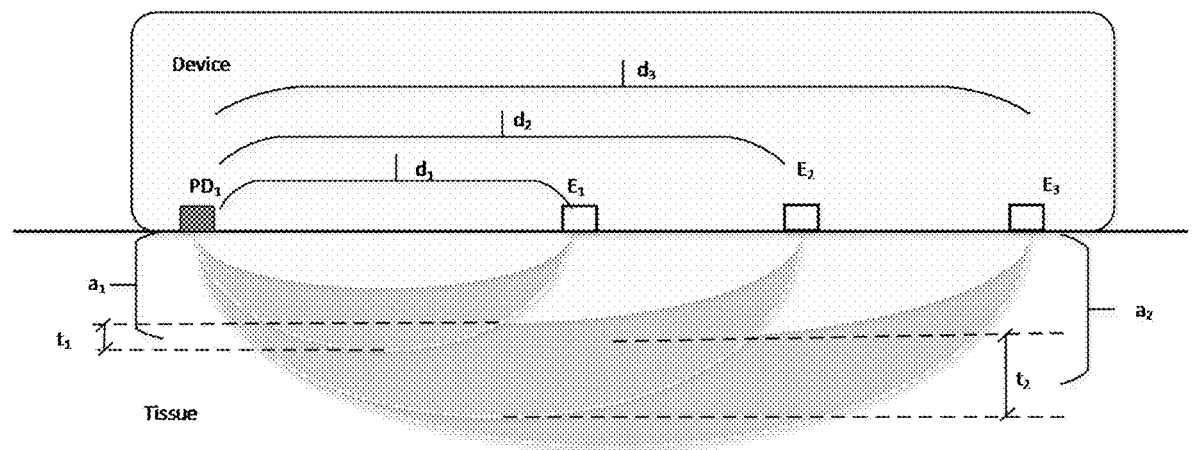
FIG. 4 is a depiction of light penetration into tissue at different depths according to an example of the present disclosure.

The ratio of the signals from two different tissue beds can be calculated in order to detect water migration between different tissue beds. This can be done, for example, by using the projection method to estimate the hydration level on each tissue layer. The projection method requires the use of two illuminator/LED spacings to estimate the composition of tissue directly below the illuminator/LED pairs. With three spacings we are able to determine the composition of tissue at two different depths, one shallower and another deeper, as depicted in FIG. 4. In this example the distribution of photons that are emitted by the illuminators ($E_1$, $E_2$ and $E_3$) and detected by the photodetector (PD) is depicted by the known "banana shapes". Three of these shapes are depicted, one for each illuminator/photodetector pair, each pair separated by a distance $d_1$, $d_2$ and $d_3$ for the $E_1$/PD, $E_2$/PD and $E_3$/PD pairs, respectively. The tissue depths of overlap between these shapes are highlighted by the dashed lines. Two overlap regions are present, the first between the first emitter ($E_1$) and the second emitter ($E_2$), probing an overlapping thickness $t_1$ at an average depth $a_1$, and the second between the second emitter ($E_2$) and the third emitter ($E_3$), probing an overlapping thickness $t_2$ at an average depth $a_2$. Given that $d_3>d_2>d_1$ we have that $t_1$ is located at a shallower depth in tissue than $t_2$, thus enabling us to probe different tissue depths using different illuminator/PD spacings.

The vector projection method utilizes measurements from two distances to estimate the tissue composition between an illuminator/PD pair. Hence, we are able to measure the hydration signal at tissue layers $t_1$ ($h_1$) and $t_2$ ($h_2$). To the extent that both layers are affected by blood volume changes the ratio $h=h_2/h_1$ is less affected by blood volume changes, thus providing us with a signal h that is more robust to blood volume changes.

Changes in posture—for example, sitting versus standing—give rise to rapid blood volume changes, especially more in peripheric (shallower) tissues than in deeper tissue since the volume of blood in the capillaries and interstitial space present in shallower tissue are more susceptible to relative changes in blood pressure. Hence, one can use the variation in the difference in hydration levels or blood volume to estimate changes in user posture. That is $\Delta h=h_2-h_1$ will increase as the user increases the position of the limb being monitored with respect to heart level and will decrease as the user decreases the position of the limb being monitored with respect to heart level. Similarly, one could estimate the blood volume in the two tissue layers and calculate $\Delta tHb=tHb_2-tHb_1$ and use it the same way as $\Delta h$ to estimate changes in posture, wherein $tHb_1$ is the blood volume calculated at average tissue depth $a_1$ using the sum of the estimates of oxyhemoglobin and deoxyhemoglobin obtained according to the projection method, and $tHb_2$ is the blood volume estimate at average tissue depth $a_2$.

The spacings $d_1$, $d_2$ and $d_3$ are fixed for a given sensor and are not customized for different users, meaning that average tissue depths $a_1$ and $a_2$ are not likely to lie at specific depths of interest in users. For example, $a_1$ could lie in a lipid layer, known for reduced water content (about 10%) while $a_2$ could lie in muscle, known for increased water content (about 80%), thus increasing the water sensitivity of the device by increasing the ratio h. Fine tuning of $a_1$ and $a_2$ (and, hence, h) can be done by using linear interpolations of the signals acquired at $a_1$ and $a_2$, resulting in signals obtained at virtual average depths $a_1'$ and $a_2'$, respectively. This results in a new hydration signal $h'=h_2'/h_1'$, where $h_1'$ and $h_2'$ are calculated at $a_1'$ and $a_2'$, respectively.

In at least one example, the present disclosure can include an optical-electronic device for determining the level of a biological indicator within tissues or blood vessels. The device can determine the existence of an extraneous factor by determining a modulus of a residual of the fit of a projection onto a matrix containing the spectra representative of a predetermined data set of one or more chromophores. According to the present disclosure, determination of the level of a biological indicator within tissue or blood vessels is achieved by calculating a relative match, or indices, between the spectral data received at the detector with a predetermined spectral data set of one or more chromophores corresponding to the biological indicator. In at least one example, the predetermined spectral data set corresponds to the signal spectra of specific analytes that can be readily obtained from the literature. See for example, Analyt. Biochem. Vol 227, pp. 54-68 (1995). The relative match calculation is performed by calculating a projection of the spectral data set captured from a user in the direction of the predetermined spectral data set in order to calculate an index that reflects the proximity of the match. The spectral projection method can be used to calculate a relative percentage level of a biological indicator or, with proper calibration, can be used to calculate the absolute concentration of a biological indicator.

The spectral projection method of determining the level of a biological indicator can be implemented mathematically using the inner product method which will be explained, by way of example, using the Total Oxygenation Index (TOI) as the biological indicator of interest. TOI is the ratio of the oxygenated hemoglobin (HbO2) to total hemoglobin (tHb), where total hemoglobin (tHb) is equal to the combined concentrations of the oxygenated hemoglobin (HbO2) and the chromophore deoxygenated hemoglobin (HHb):

TOI=[HbO2]/[tHb] or TOI %=100*([HbO2]/[tHb]), where [tHb]=[HbO2]+[HHb].

TOI, as used herein, includes the more specific parameter, SmO2, which is the muscle oxygen saturation. SmO2 can also be the tissue oxygen saturation determined from optical measurements of muscle tissue. Both oxygenated hemoglobin (HbO2) and deoxygenated hemoglobin (HHb) are chromophores for which a spectral data set can be predetermined. The notation O(D) can be used to denote the predetermined spectral data for oxyhemoglobin (deoxyhemoglobin) at the same wavelengths for which the spectral data set for a user was measured at the detector, and U can be used to denote the measured data set, including an effective attenuation ($\mu_{\mathit{eff}}$) or an effective absorption coefficient ($\mu_a$). The inner product method of calculating the spectral projection can be calculated according to different mathematical methods, including, but not limited to, a direction cosine method, vector projection method, and a pseudo-inverse projection method:

Direction Cosine Method:

$$TOI = \frac{\langle U, O \rangle}{\left\langle U, O+D\sqrt{\frac{\langle O, O \rangle}{\langle D, D \rangle}} \right\rangle},$$

Vector Projection Method:

$$TOI = \frac{\langle U, O \rangle}{\left\langle U, O+D\frac{\langle O, O \rangle}{\langle D, D \rangle} \right\rangle},$$

Pseudo-Inverse Projection Method:

$$TOI = \frac{\left\langle U, O - \frac{\langle O, D \rangle}{\langle D, D \rangle}D \right\rangle}{\left\langle U, O\left[1 - \frac{\langle O, D \rangle}{\langle D, D \rangle}\right] + D\left[\frac{\langle O, O \rangle}{\langle D, D \rangle} - \frac{\langle O, D \rangle}{\langle D, D \rangle}\right] \right\rangle}.$$

All of these methods can be rewritten as $$TOI = \frac{\langle U, O - aD \rangle}{\langle U, O(1-a) + D(b-a) \rangle}$$

where a and b are scalars defined as i) $a = 0, b = \sqrt{\frac{\langle O, O \rangle}{\langle D, D \rangle}}$;

ii) $a = 0, b = \frac{\langle O, O \rangle}{\langle D, D \rangle}$; and iii) $a = \frac{\langle O, D \rangle}{\langle D, D \rangle}$ and $b = \frac{\langle O, O \rangle}{\langle D, D \rangle}$ for the cosine, vector projection and pseudo-inverse methods, respectively.

In at least one example, the present disclosure includes use of the projection method to detect additional chromophores that do not vary as a function of hydration or blood volume variations. For example, collagen, lipid and cytochrome oxidase, melanin or even, to a lesser extent, total hemoglobin. The absorption spectra of these anchor materials are included in the tissue absorption matrix before calculating its pseudo-inverse. Therefore, the concentration of these chromophores can be estimated and the estimates can be used to anchor other measurements, for example hydration. In one example, the concentration estimate of one or more of these anchor chromophores can be y, then the new hydration estimate $h_y$ is given by $h_y = h_2/y$. That is, the new hydration estimate, $h_y$, is given by $h_2$, the original hydration estimate at average depth $a_2$ (known to be less affected by blood volume changes) divided by the estimate of the concentration of one or more of the anchor chromophores, y. In the case of collagen and lipid, for example in FIG. 5, the absorption peaks are close to each other within the range of detection of Silicon photodiodes (910 nm and 1020 nm for collagen and 930 nm and 1040 nm for lipid). Therefore, distinguishing between the two chromophores is difficult, but both collagen and lipid are not likely to change significantly within the time range of interest (from 1 second to 8 hours). Therefore, the two chromophores can be considered to be a single compound anchor chromophore, evaluated by quantity y and detected by using illumination sources (LEDs) with peak wavelengths centered close to 920 nm and 1030 nm.

Also note that other ratios of interest could be used. For example, the ratio of ratios, $(h_1/y_1)/(h_2/y_2)$ can be used to estimate the relative change of hydration with respect to different layers while anchoring the estimate with respect to a chromophore with a slowly varying concentration, wherein $y_1$ and $y_2$ denote the chromophore estimated concentrations at depths $a_1$ and $a_2$, respectively. The interpolations, for example, can be combined to customize the hydration measurement to a given user and thus calculate hydration as $(h_1'/y_1')/(h_2'/y_2')$, wherein $y_1'$ and $y_2'$ are the estimated concentrations at virtual depths $a_1'$ and $a_2'$, respectively.

The depths $a_1$ and $a_2$ can be operable for enhanced hydration monitoring depending on the tissue bed underneath the sensor. For example, over large skeletal muscles $a_1$ can be set at the depth of the lipid layer while $a_2$ can be set at the depth of muscle. In another example, in anatomical locations without large skeletal muscles, for example, the wrist, $a_1$ can be set at the depth of the epidermis while $a_2$ can be set at the depth of the lipid layer. In another example, in anatomical locations that have skeletal muscle tissue but not a significant lipid layer, such as the forearm, $a_1$ can be set at the depth of epidermis while $a_2$ can be set at the depth of muscle. Furthermore, in anatomical locations that lack significant lipid or muscle layers, such as the temple or forehead, $a_1$ can be set at the depth of at least one of the epidermis or bone while $a_2$ can be set at the depth of at least one of subarachnoid space, cerebral spinal fluid or gray matter. This last configuration uses the water content of the head and, specifically, the brain, to monitor overall body hydration and benefits from the human body autoregulation to render a hydration measurement that is less affected by blood volume variations.

Figure 5:
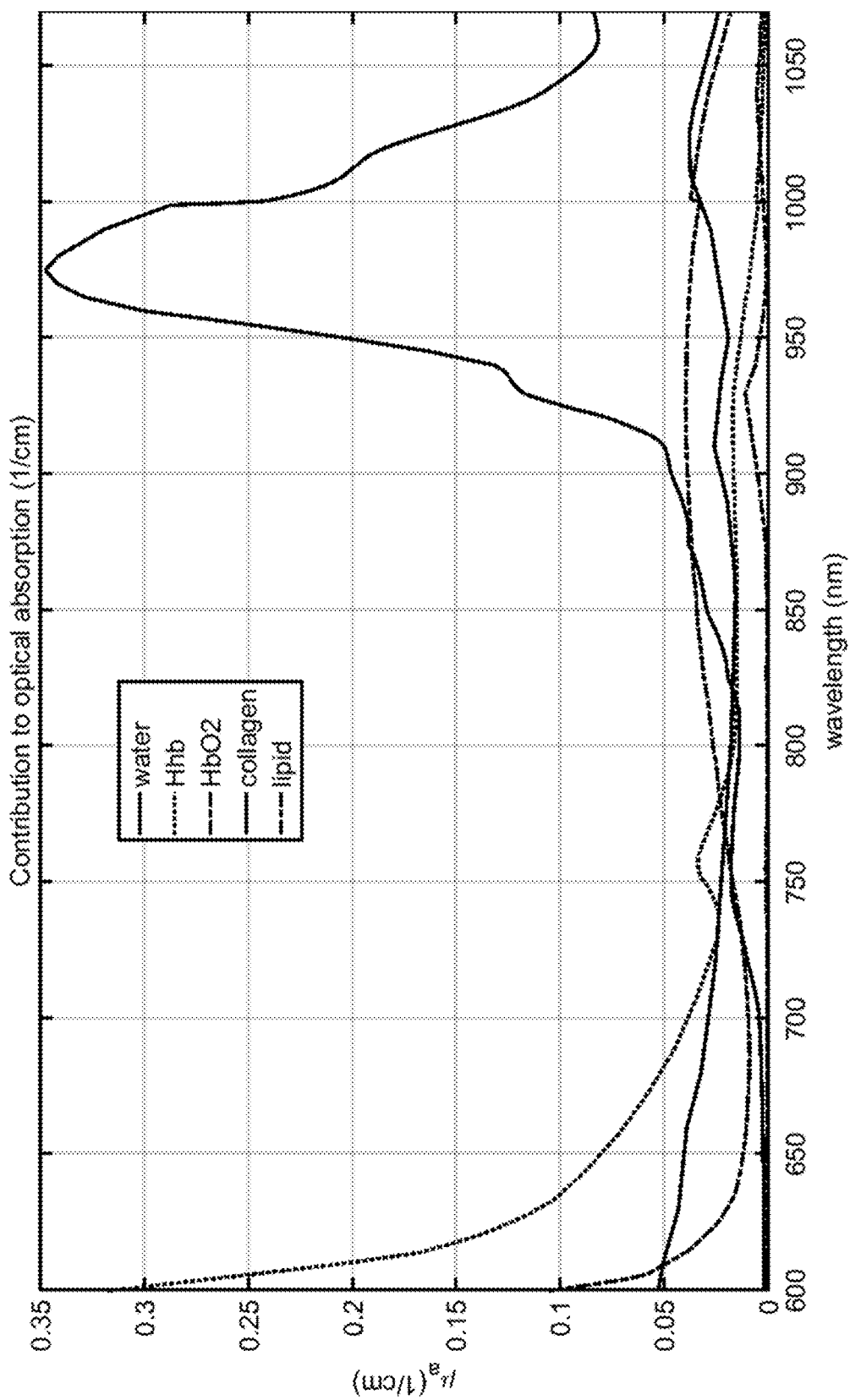
FIG. 5 is a plot of the absorption coefficients of oxyhemoglobin, deoxyhemoglobin, collagen, lipid and water within the range from 600 nm to 1075 nm.
Figure 6:
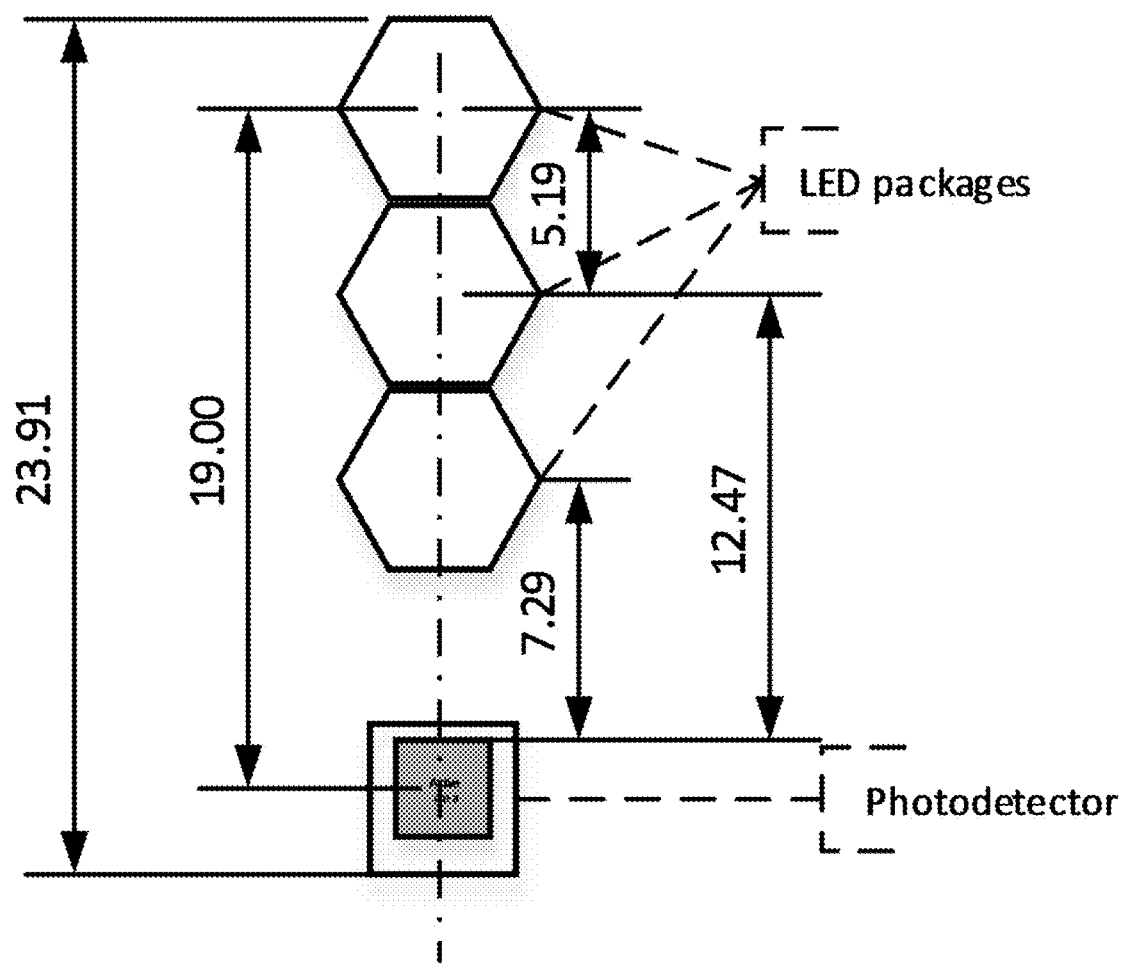
FIG. 6 is a depiction of the arrangement of LEDs and photodiodes according to another example, being an implementation for use on the wrist, of the present disclosure.

The sensor geometry can be dependent on the depth of tissue layers that lie underneath the sensor. Hence, when the sensor is used on the wrist, the sensor is operable such that the geometry can encompass reduced spacings between the illuminator/PD pairs given the reduced averaged depths of tissue layers in that site compared to large skeletal muscles. The diagram in FIG. 5 shows the example of a geometry for use on the wrist in which the spacings $d_1$, $d_2$ and $d_3$ are approximately 7 mm, 12 mm and 18 mm, respectively. The reduced spacings also result in a more compact device, more suitable and comfortable for use on the wrist.

FIG. 2 depicts a lateral cross-section of a wearable device 100 used for hydration monitoring having a controlled pressure to regulate a hydration level of a tissue underneath a sensor. The wearable device can include: an emitting component 102, a sensor 104, and a processor. In an example, the emitting component 102 can be operable to emit light having at least three different wavelengths, where at least one of the wavelengths is in the range from 900 nm to 1600 nm for optical detection of a level of water. In one example, at least one of the wavelengths may be in the range from 900 nm to 1200 nm. The emitting component 102 can include a glass or epoxy enclosure or channel 108 and multiple light emitting diodes (LEDs) 110 for emitting the at least three different wavelengths. The sensor 104 can be operable to receive a reflected portion of the emitted light from the emitting component 102. The processor can be on a printed circuit board 106 to which the emitting component 102 and the sensor 104 are connected.

The device 100 can further include a recessed cavity 111 to avoid excess pressure, a layered material 112 capable of wicking moisture away from the sensor, and at least one breathing channel 114 to aerate a space between the sensor and the skin. The layered material 112 can be removable or disposable. The breathing channel 114 can be at least one of a capillary tube, an angulated air channel, and micro-holes. In an example, the layered material 112 can have at least two layers, where the first layer is a breathable polymer layer 116, and the second layer is a wicking layer 118. For example, the breathable polymer 116 layer can be polyethylene and the wicking layer 118 can be Lycra®. Alternatively, both layers can be comprised of a compound fabric. For example, the compound fabric can be the Sontek® breathable fabric by Fatra. (Fatra a.s., Czech Republic). In another example, the layered material can be a 3-layered material, where a first layer comprises an adhesive, a second layer comprises a wicking material, and a third layer comprises a water-absorbing material. The fabric can be removable or disposable in some examples.

In an example, the processor is operable to receive signals from the sensor and to calculate a vector projection selected for hydration monitoring. In another example, the processor is operable to receive signals from the sensor and to calculate a regression to determine at least one of a blood volume level and/or a hydration level. The sensor 104 can be a photodetector operable to receive a reflected portion of the emitted light from the emitting component 102. The at least three distances between the light emitting component 102 and the photodetector 104 are known, and the at least three distances allow monitoring of at least two different tissue beds with at least two different tissue depths. The at least two different tissue beds can include one tissue bed that is a shallow tissue bed and another tissue bed that is a deep tissue bed. For example, the shallow tissue bed can be selected from a lipid, an epidermis, and bone and the deep tissue bed can be selected from a muscle, a lipid, a subarachnoid space, a cerebral spinal fluid, or gray matter. The processor can further be operable for calculating the ratio of signals from the different tissue beds. In an example, one of the at least two different tissue depths is used as a reference. The device 100 can further be operable to detect a slowly-varying analyte, where the slowly varying analyte is one or more of collagen, lipid, cytochrome oxidase, melanin, or total hemoglobin. The processor can then be further operable for adapting a weighting of the wavelengths dynamically to remove interference that varies over a time interval substantially shorter than that of the slowly varying analyte.

Figure 7:
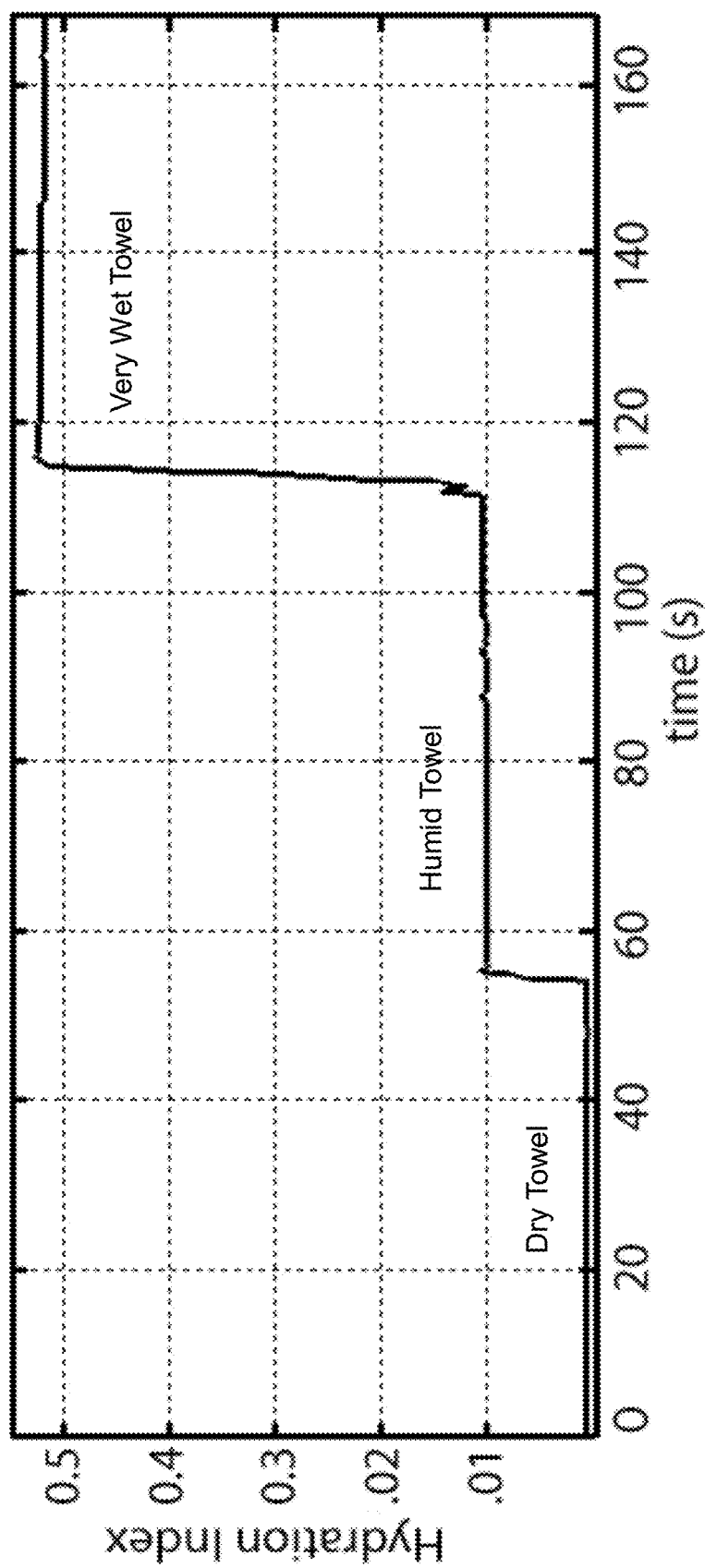
FIG. 7 is a graph depicting differing hydration index values for different types of towels as the device is placed on the different types of towels over time.

FIG. 7 illustrates a device operable according to the present disclosure placed on a dry towel, a humid towel, and a very wet towel. As illustrated, the hydration index for a wet towel is below a zero reading. The humid towel is at the zero reading and a very wet towel is at the 0.4 reading. The illustration of FIG. 7 indicates that the device is clearly able to detect differing hydration levels with a very favorable signal-to-noise ratio.

Figure 8:
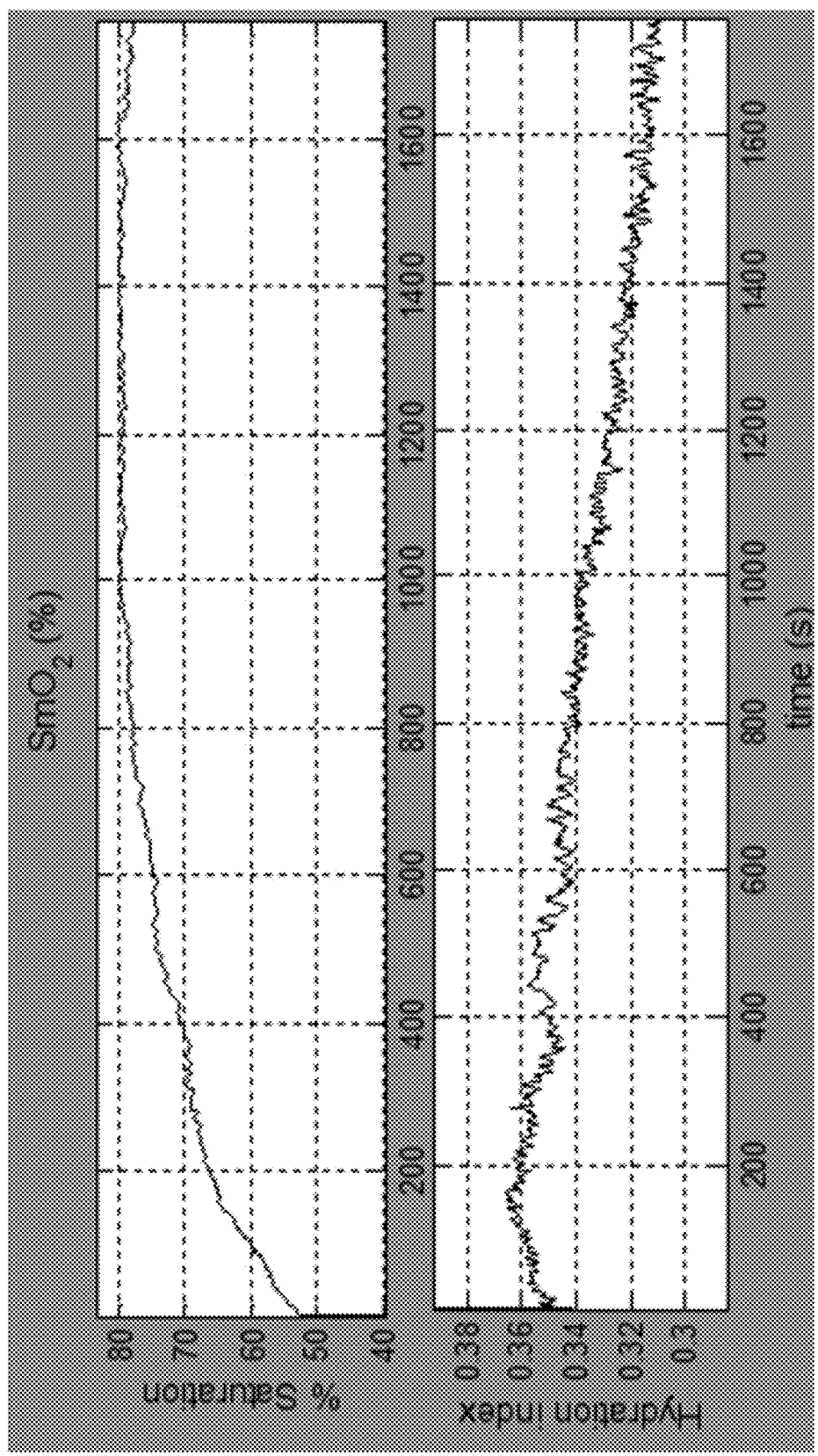
FIG. 8 is an example of a chart of percent of saturation and hydration index versus time.
Figure 9:
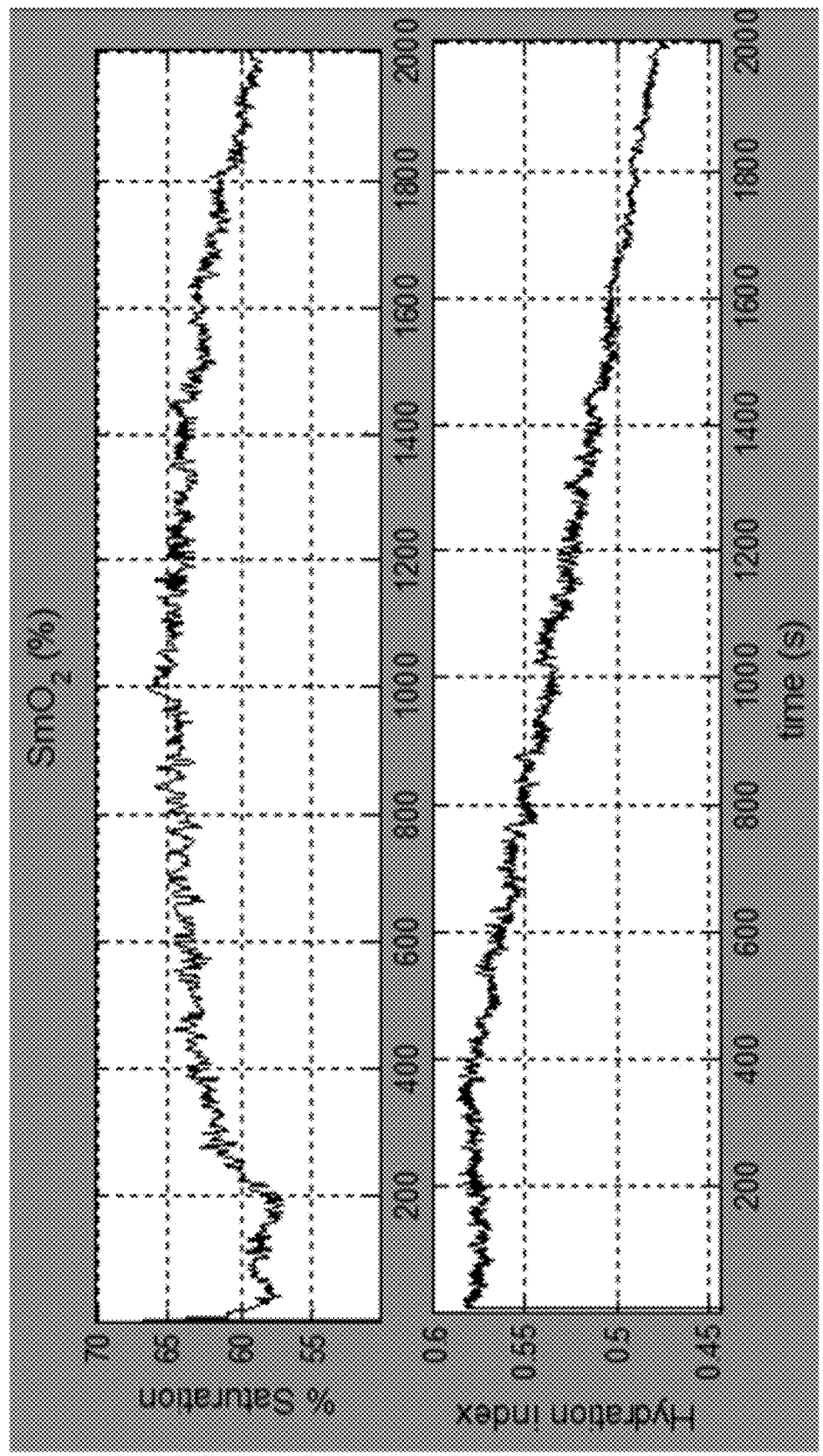
FIG. 9 is another example of a chart of percent of saturation and hydration index versus time.
Figure 10A:
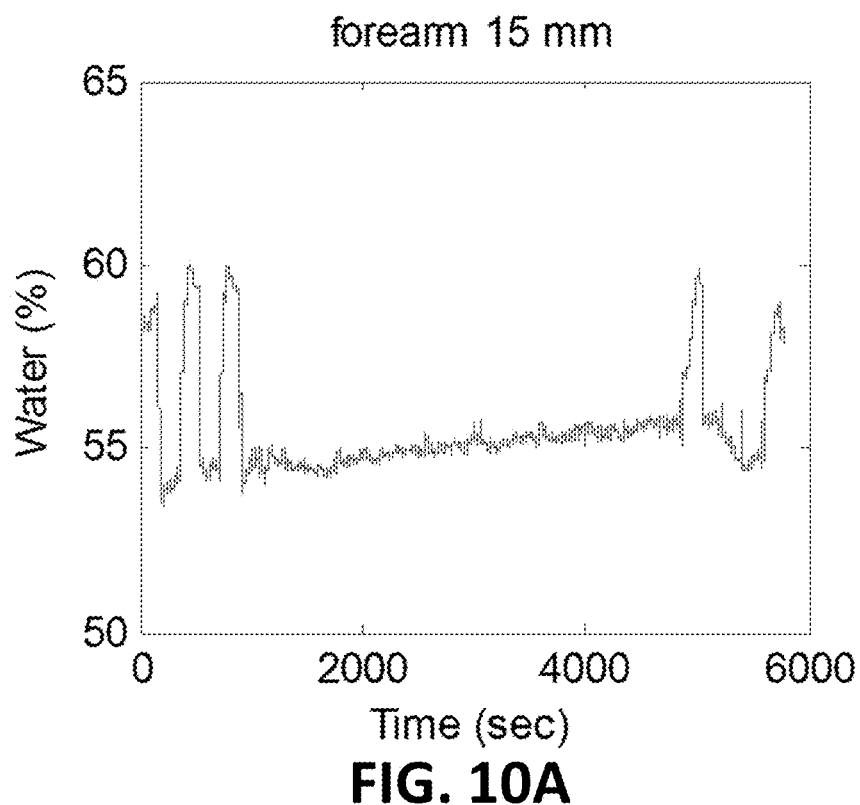
FIG. 10A is a chart applying the linear regression model according to the present disclosure to experimental data for the forearm at 15 mm to correct for blood volume variations.
Figure 10B:
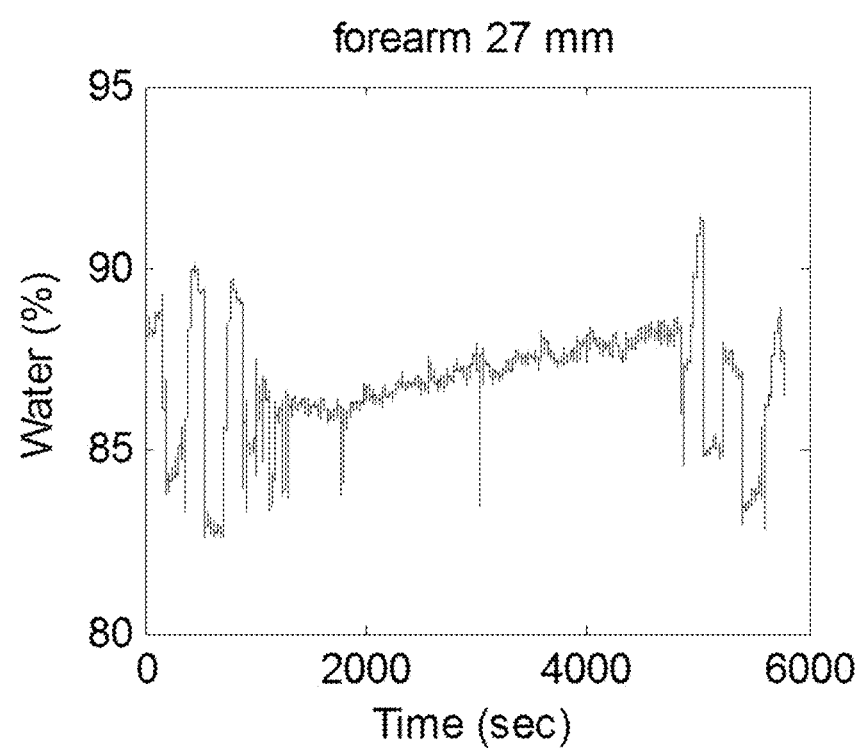
FIG. 10B is a chart applying the linear regression model according to the present disclosure to experimental data for the forearm at 27 mm to correct for blood volume variations.
Figure 10C:
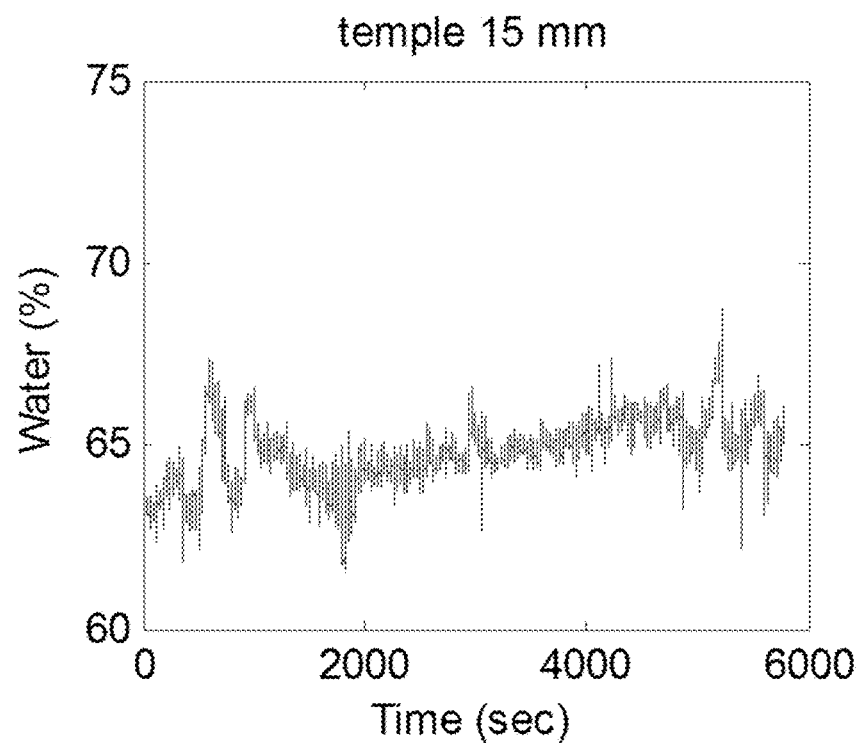
FIG. 10C is a chart applying the linear regression model according to the present disclosure to experimental data for the temple at 15 mm to correct for blood volume variations.
Figure 10D:
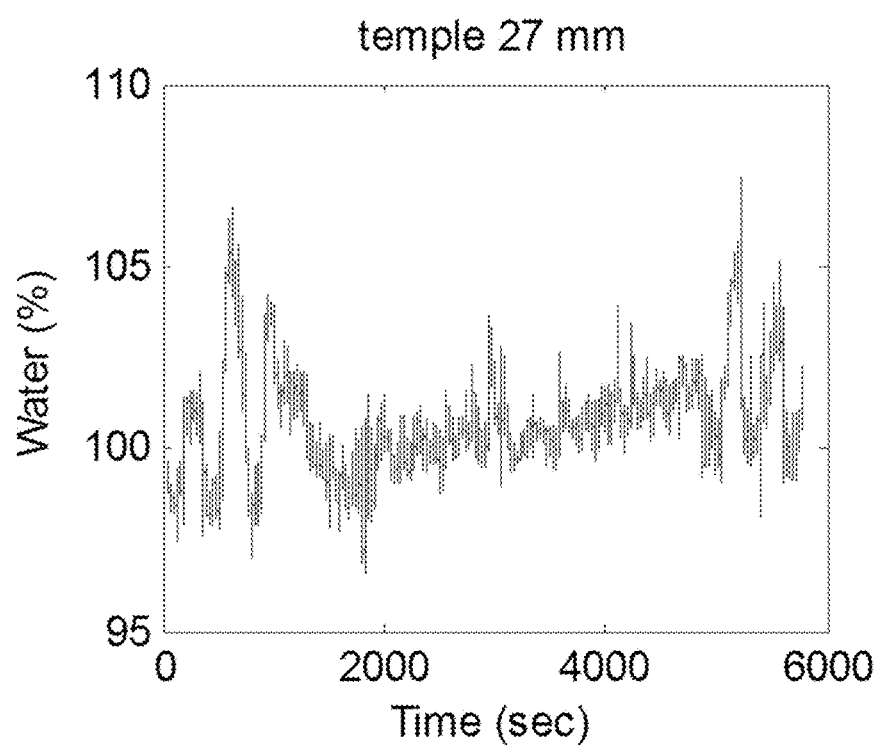
FIG. 10D is a chart applying the linear regression model according to the present disclosure to experimental data for the temple at 27 mm to correct for blood volume variations.

FIG. 8 illustrates a plot of percentage of saturation over time and the hydration index over time during an exemplary lactate threshold assessment while FIG. 9 illustrates a plot of percentage of saturation over time and the hydration index over time during a second exemplary lactate threshold assessment. Lactate threshold assessments consist of physical exercise ramps of increasing effort (running or cycling) in which the subject starts at a leisure pace and increases his/her pace in 3-minute increments until reaching exhaustion at the end of the assessment. Assessments are usually designed to last from 20 to 30 minutes and result in an initial increase in muscle oxygenation followed by a plateau and a decrease in oxygenation once the subject surpasses his/hers lactate threshold. Also, if a subject abstains from ingesting liquids at least two hours before the assessment (and during the assessment) his or her hydration level tend to decrease over time, especially in later stages of the assessment when the subject core temperature has increased as a result of increased physical exercise, resulting in tissue water loss through perspiration. The hydration index plots shown in the bottom of FIGS. 8 and 9 initially show little variation in hydration levels up to 400 s, followed by a continuous decrease in hydration after 400 s. This corresponds to the expected behavior given the limited physical effort associated with the first two stages of lactate threshold assessments, followed by increasingly higher efforts—and increased core body temperatures and water loss through perspiration—associated with the later stages of lactate assessments.

FIG. 10 is a chart applying the linear regression model according to the present disclosure to experimental data to correct for blood volume variations.

Figure 11:
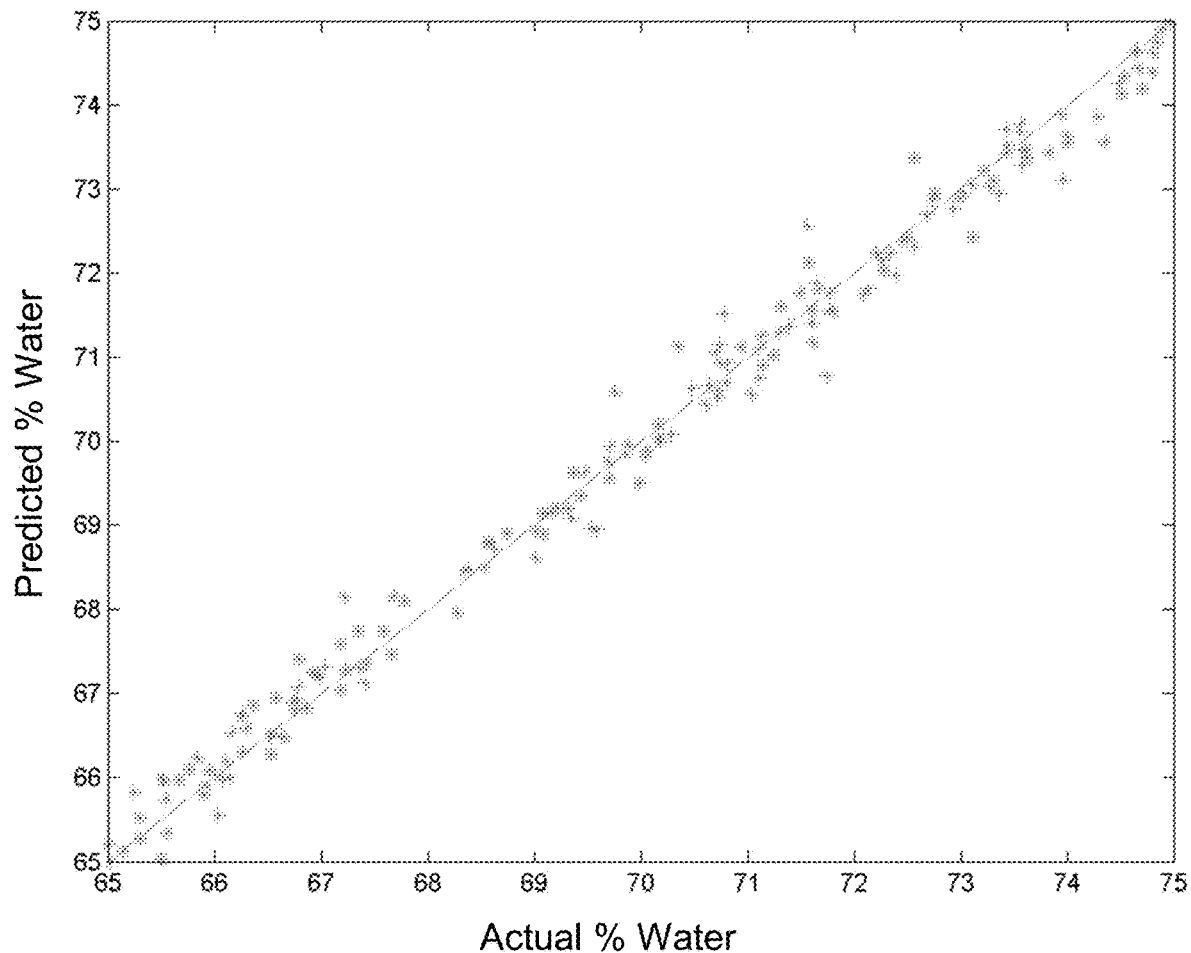
FIG. 11 is a correlation plot showing the relationship between the predicted hydration signal versus the actual tissue hydration for simulated skin tissue composed of various amounts of blood, collagen, and lipid.

FIG. 11 illustrates a correlation plot showing the relationship between the predicted hydration signal versus the actual tissue hydration. A predicted hydration signal was obtained using the multiple linear regression method. A range of actual hydration levels was obtained by simulating a range of tissues using a Monte-Carlo simulation. Additionally, at a given hydration level, other parameters were varied, including blood volume, blood oxygenation level and collagen and lipid concentrations.

Figure 12:
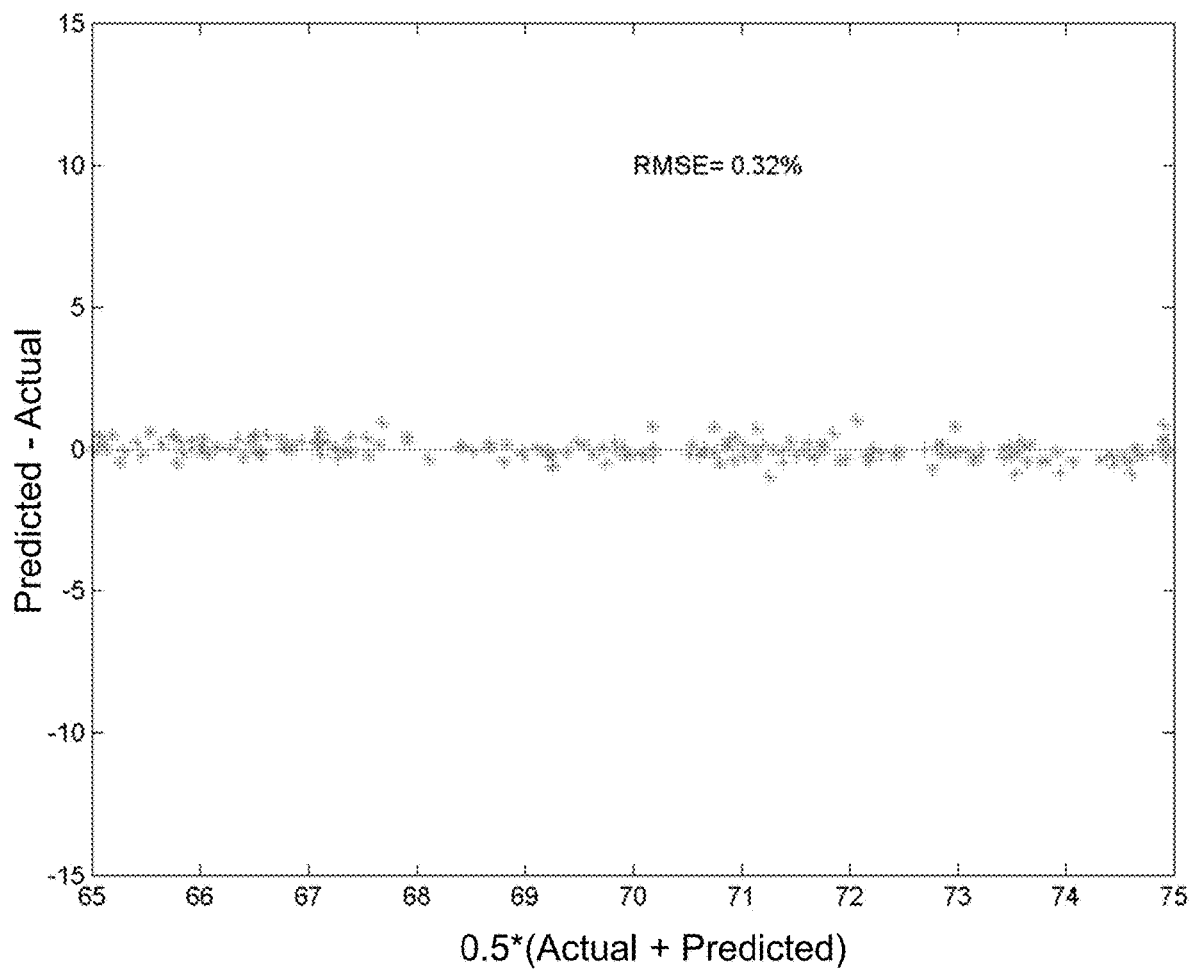
FIG. 12 is a Bland-Altman plot of the difference between the predicted and actual percentage of water in the simulated skin tissue.

FIG. 12 illustrates a Bland-Altman plot corresponding to the error of the predicted hydration signal versus the actual tissue hydration in FIG. 11.

Figure 13:
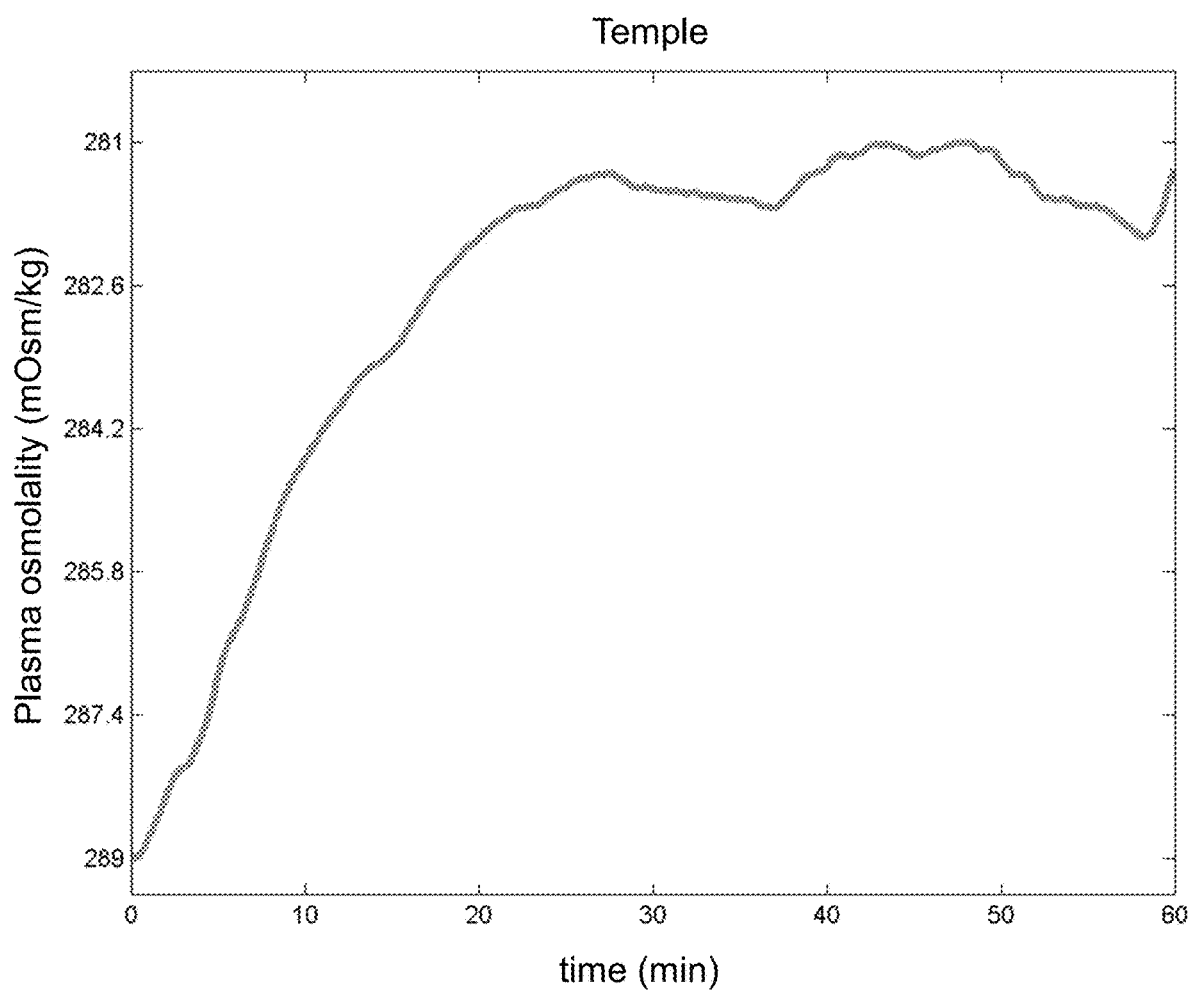
FIG. 13 shows the hydration index measured on the temple of a subject during rehydration using the vector projection method.

FIG. 13 illustrates the hydration index measured using the vector projection method during rehydration. In the illustrated example, a subject started in a dehydrated state and drank about 1 L of water a few minutes before time=0. Plasma osmolality measurements were performed in the dehydrated and euhydrated states and were used to calibrate hydration index (inverted scale on the vertical axis). The device was applied to the temple of the subject, demonstrating that method is not limited to sites with muscle tissue.

Figure 14:
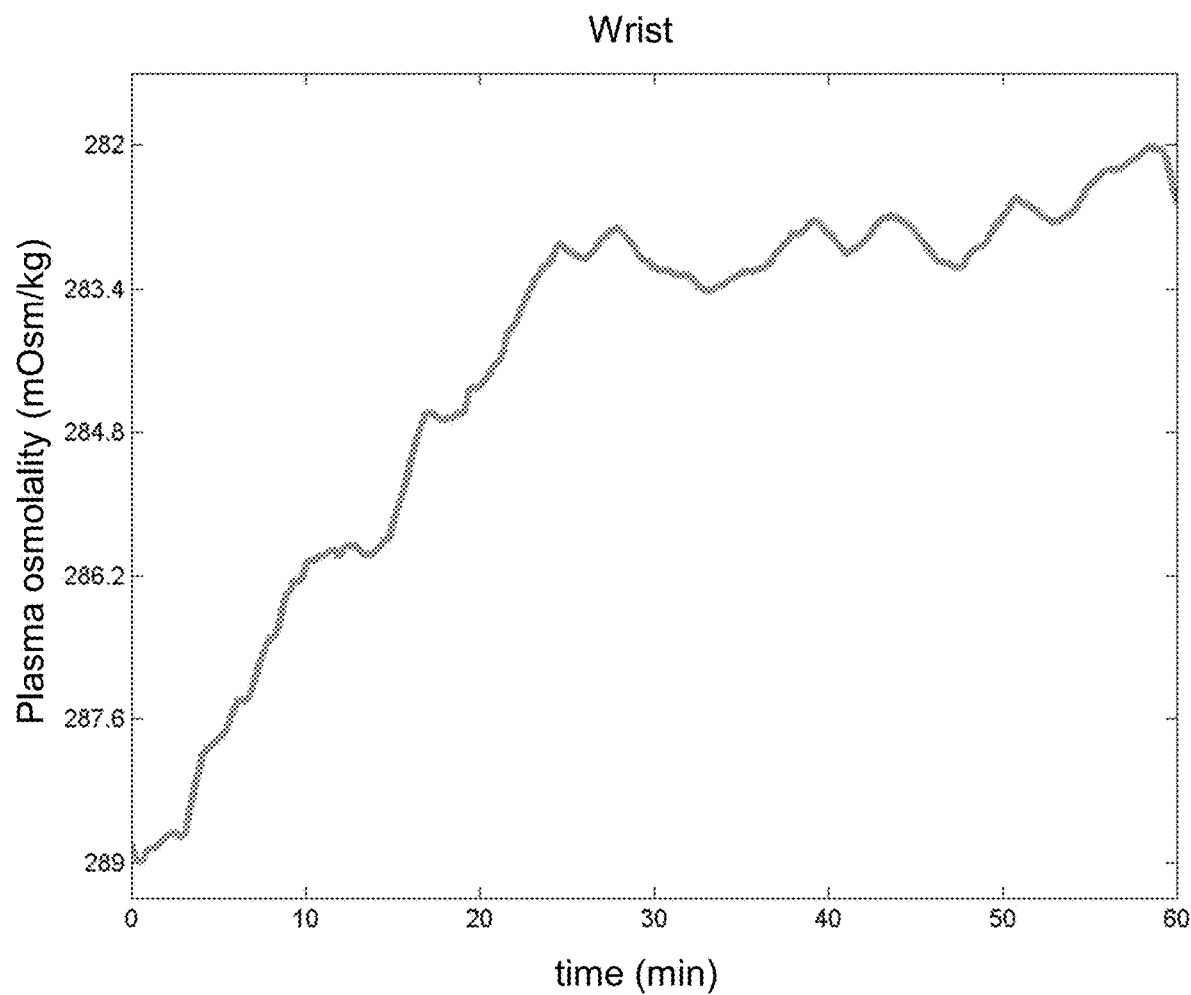
FIG. 14 shows the hydration index measured on the wrist of a subject during rehydration using the vector projection method.

FIG. 14 illustrates the hydration index measured using the vector projection method during rehydration. A subject started in a dehydrated state and drank about 1 L of water a few minutes before time=0. Plasma osmolality measurements were performed in the dehydrated and euhydrated states and were used to calibrate hydration index (inverted scale on the vertical axis). The device was applied to the wrist of subject, demonstrating that method is suitable for monitoring hydration in the wrist.

Additional examples will be described in relation to tests that were performed to assess hydration including the use of the device as described above.

Analysis of data from this trial confirmed that site-to-site and subject-to-subject variations in blood volume pose the main challenges to quantitative hydration measurement. The differences observed at 27 mm and 15 mm suggest that a larger change in blood volume occurred in the superficial dermis than in deeper dermis and muscle at several sites. Blood pooling due to hydrostatic pressure was likely to be responsible for the differences observed between upper-body (for example, temple, pectoral, or wrist) and lower-body trends in the optical densities (ODs) at the individual wavelengths.

To view overall trends of the processed data on a hypothetical "average" subject, the following normalization procedure was used: set the baselines of the OD data obtained from the same site on all subjects to zero at a certain reference time (for example, time at which hydration began) and average the normalized cross-subject OD values at each wavelength. The result is an average trend curve for each LED channel, which can be processed to observe the $Hb_T$, SmO2, and hydration trends. In contrast to all of the other wavelengths, attenuation at 665 nm tended to decrease at most sites, except the wrist. When oxygen saturation is high, absorption at 660 nm is very low. The downward trend resulted from an increase in oxygenation of venous blood, due to opening of A-V shunts as blood perfusion improved during rehydration. A decrease in scattering, which has a greater effect when absorption is low, is also present.

The mechanical design of the sensor's interface with the skin is an important consideration. For the sensors placed on the calf and wrist, a trend reversal in optical attenuation was evident midway through the study. The reversal may be related to an increase in skin compression by the sensor.

The optical data obtained from the wrist was the least stable, because of the inhomogeneous nature of the tissue below the skin (for example, in ligaments, blood vessels, nerves, etc.), which made the measurements more susceptible to motion artifacts. Subdermal muscle at other sites provides better mechanical and optical stability. If a location on the proximal wrist distal to the belly of the muscles in the forearm is to be considered a candidate for hydration assessment, the source-detector separation (for example, <5 mm) should be minimized to confine the photon paths to the dermis.

One of the first considerations in the design of the hydration sensor is which spectral region to choose for water measurement. The table below summarizes the advantages and disadvantages of the different spectral regions.

| Spectral Band | Advantages |
| --- | --- |
| Short-λ VIS (450-600 nm) | Better confinement of light to dermis for short s-d spacing. High optical contrast between Hb, HbO2, and background tissue. Inexpensive LEDs and photodiodes available. |
| Red - SWNIR (600-1100 nm) | Inexpensive LEDs and photodiodes available. Water absorption band at 970 nm. Lipid and collagen absorption bands on both edges of the water absorption band can serve as references. |
| NIR (800-1600 nm) | Water absorption exceeds Hb/HbO2 absorption at wavelengths longer than 1200 nm. Multiple water, lipid, and protein absorption bands. |

Overall, for algorithm development, the 800-1600 nm band is the most information-rich and may even enable absolute hydration measurement across users. However, since the cost constraints and compatibility with other measurements are overriding constraints, the 600-1100 nm band is the next best choice. The water absorption bands is strong enough to permit, at least, user-specific trending, provided that robust methods for suppressing the effects of blood volume variations can be developed.

Additionally, prevention of moisture accumulation below the sensor and optimization of skin compression are important considerations. If the body of the sensor seals the skin and is impermeable to water vapor, sweat will accumulate and 'waterlog' the epidermis. Elevated temperature below the sensor can cause blood flow in the superficial dermis to increase over time as the arteriovenous shunts in the capillary bed open in an attempt to increase evaporative losses. To mitigate this problem, either the sensor can be made 'breathable' by providing channels for air to circulate and water vapor to escape or a washable/disposable wicking layer can be sandwiched between the bottom of the sensor and the skin. If a wicking layer is employed, the optical design of the sensor will need to be modified to ensure good optical contact with the skin, while preventing shunting of light through the wicking layer.

The approach presented below employs a photon diffusion model that simulates the tissue spectra of a wide variety of subjects. The models build on MATLAB subroutines. The tissue spectra are generated by assuming that the percent composition of the main optically absorbing constituents of tissue—blood (Hb/HbO2), water, collagen, and lipid—vary over specified ranges. The percentage ranges are assumed to have a normal distribution with a certain mean and standard deviation.

In simulations, 500-2000 simulated tissue spectra were generated, representing measurements from a large number of subjects. Since the initial goal was not to achieve absolute calibration of water content across subjects, the magnitude and wavelength-dependence of the scattering coefficient was assumed to be fixed in most simulations. Then, the percent tissue water predicted by a specific algorithm was regressed against the actual water percent. The algorithm with the least root-mean-squared error (RMSE) when applied to the entire set of simulated spectra was presumed to perform best.

Linear regression of optical density at multiple wavelengths, which takes the general form, $$\% \; W = b_0 + b_1 \log(1/R_{\lambda 1}) + b_2 \log(1/R_{\lambda 2}) + \ldots + b_M \log(1/R_{\lambda M}),$$

where $b_m \log(1/R_{\lambda m})$ is the weighted optical density associated with the diffuse reflectance measured in mth of M spectral bands. In one set of simulations, a simple non-linear regression was used that introduces a normalization of the weighted optical densities by the average of all of the optical densities within all M bands measured at time $T_0$:

$$\% \; W = b_0 + b_1 \frac{\log(1/R_{\lambda 1})}{\frac{1}{M} \sum_M \log(1/R_{\lambda m})} + b_2 \frac{\log(1/R_{\lambda 2})}{\frac{1}{M} \sum_M \log(1/R_{\lambda m})} + \ldots + b_M \frac{\log(1/R_{\lambda M})}{\frac{1}{M} \sum_M \log(1/R_{\lambda m})}$$

This type of normalization is intended to reduce the effect of baseline shifts related to variations in blood volume and scattering.

Other forms of the prediction equation can be conceived, for example, $$\% \; W = \frac{b_0 + b_1 \log(1/R_{\lambda 1}) + b_2 \log(1/R_{\lambda 2}) + \ldots + b_M \log(1/R_{\lambda M})}{a_0 + a_1 \log(1/R_{\lambda 1}) + a_2 \log(1/R_{\lambda 2}) + \ldots + a_N \log(1/R_{\lambda N})}$$

Here, the denominator could represent, for example, the prediction equation optimized for measurement of the sum of collagen and lipid in the tissue.

Figure 15:
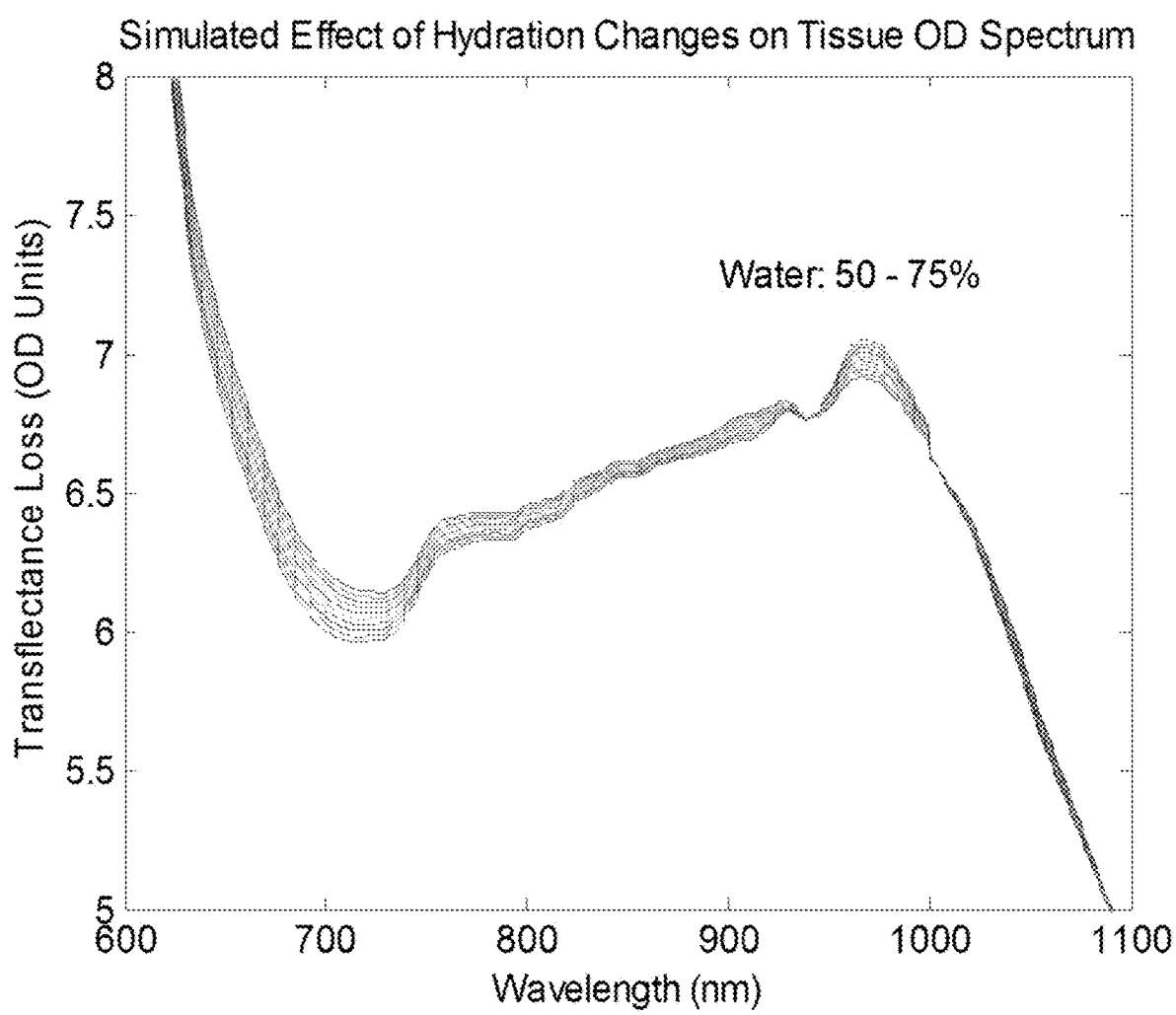
FIG. 15 illustrates simulated changes in the diffuse reflectance spectrum of skin as the water content of skin varies, with blood volume fixed.

The results are shown in FIG. 15, with the reflectance plotted in optical density units, OD=−log (1/R). Notice that not only does the OD increase with water content in the vicinity of the water absorption band between 950 and 1000 nm, but it also decreases over a wide range between 600 and 900 nm. The decrease in OD results from the displacement of collagen and lipid by water on a volumetric basis.

FIG. 15 illustrates simulated changes in the diffuse reflectance spectrum of skin as the water content of skin varies from 50 to 75%, with blood volume fixed at 5%. Thin, collimated source and detector beams were assumed, with a 1 nm detection bandwidth and a source-detector spacing of 14 mm. The dry fraction of lipid to collagen ration was fixed at 28:72%.

Figure 16:
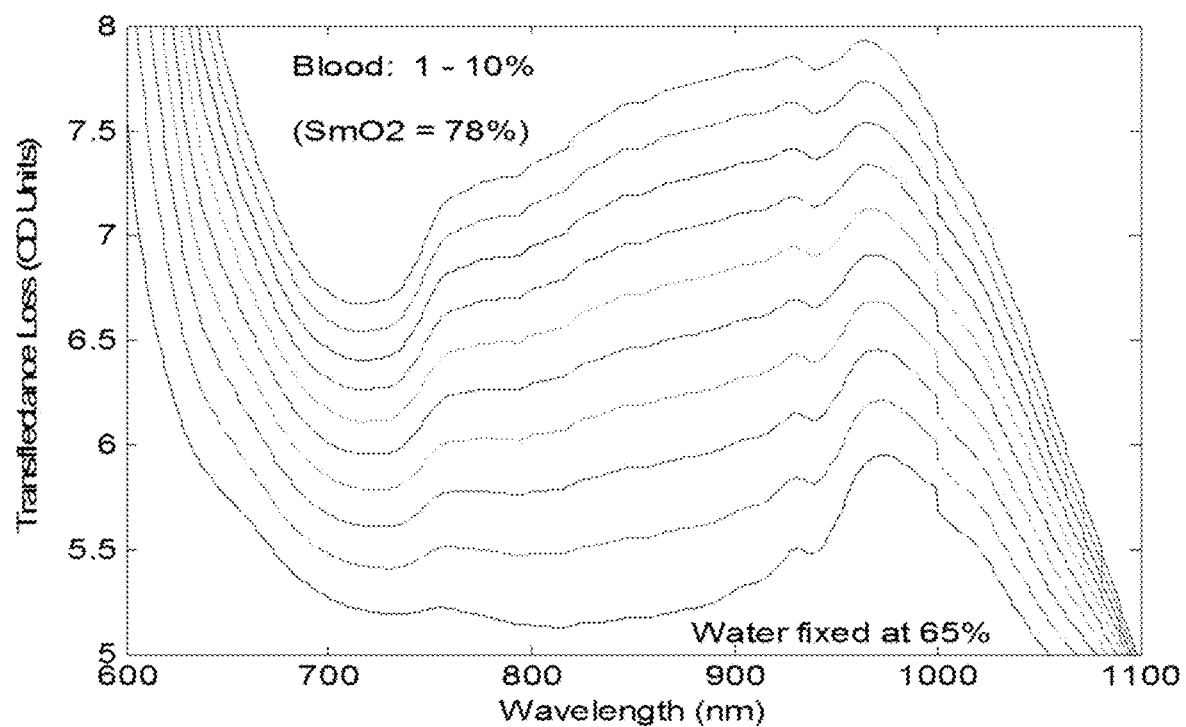
FIG. 16 illustrates simulated changes in the diffuse reflectance spectrum of skin as the blood content of skin, with water content and blood oxygen saturation fixed.

For comparison, the expected changes in the diffuse reflectance spectrum of skin were simulated for a fixed water content (65%) and a variable blood content (1-10%) at a fixed oxygen saturation (78%). The results are shown in FIG. 16. Changes in blood volume have a much larger effect on the reflectance spectrum of the skin than changes in water content. The main effects are a large upward shift in the baseline of the spectrum and a moderate increase in slope with wavelength.

FIG. 16 illustrates simulated change in the diffuse reflectance spectrum of skin as the blood content of skin varies from 1 to 10%, with water content and blood oxygen saturation fixed at 65% and 78%, respectively. Thin, collimated source and detector beams were assumed, with a 1 nm detection bandwidth and a source-detector spacing of 14 mm.

Subsequent investigations focused on wavelength selection using multiple linear regressions. An exhaustive search yielded as set of wavelengths (820, 920, 960 nm) on the short-wavelength edge of the 970 nm water band. Use of narrowband sources instead of LEDs permits effective use of differential absorption measurements at multiple wavelengths between the water and lipid/collagen absorption bands.

Figure 17A:
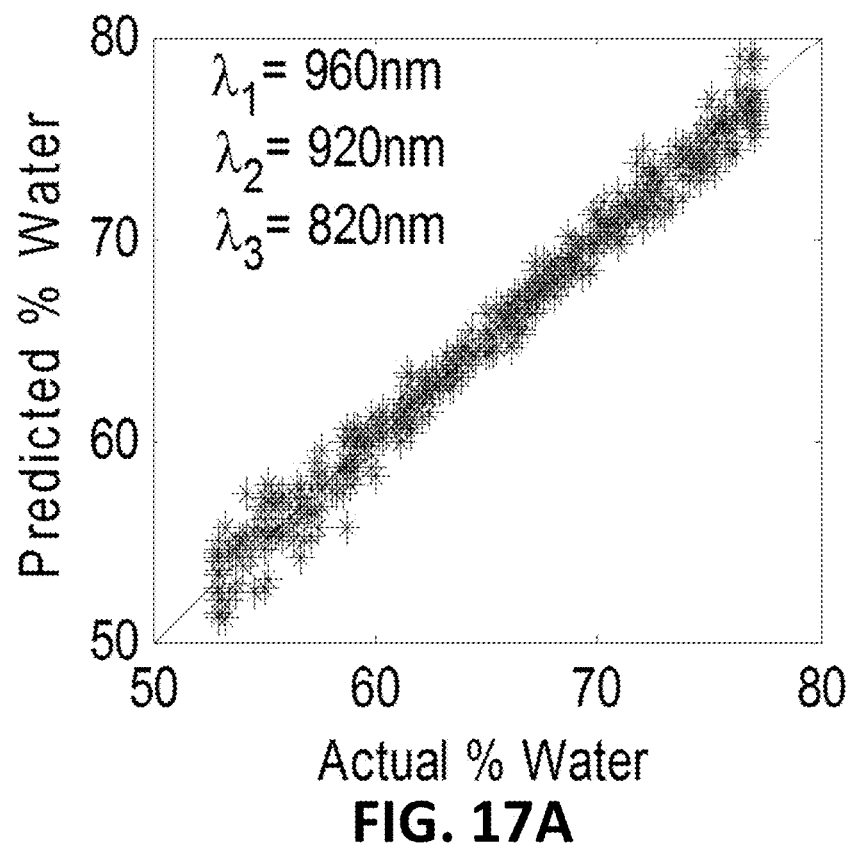
FIG. 17A illustrates tissue water content predicted by linear regression, using the equation % W=128 OD$\lambda_1$−267 OD$\lambda_2$+164 OD$\lambda_3$, for a combination of three narrowband (for example one nm) light sources.
Figure 17B:
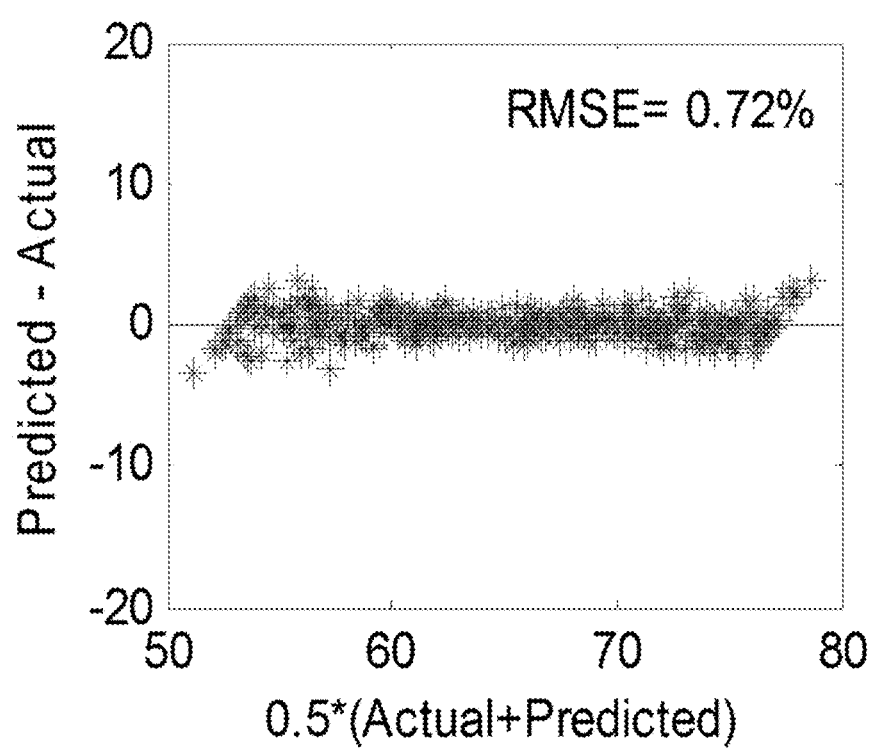
FIG. 17B illustrates the difference between predicted and actual % water from FIG. 17A.

FIG. 17 illustrates tissue water content predicted by linear regression (as illustrated using, the equation at the bottom of the figure) for an optimal combination of three narrowband (for example, 1 nm) light sources. For these simulations, the mean blood volume in the tissue was assumed to equal 5%, with a standard deviation of +/−2%. Thin, collimated source and detector beams were assumed, with a source-detector spacing of 14 mm.

Although custom semiconductor lasers are readily available in the 780-980 nm spectral band, their expense may not be justified by the improvement in accuracy that can be achieved versus LEDs.

The next set of investigations focused on finding optimal combinations of LEDs for tissue water measurement. Exhaustive searches were performed all possible combinations of LEDs chosen from a set of seven available LEDs with center wavelengths equal to 665, 810, 850, 950, 970, 1020, and 1050 nm.

The dual-LED combination (850, 950 nm) yielded a poor RMS prediction error (2.66%). The RMS prediction error decreased significantly as the number of LED wavelengths increased: 1.73% for optimum 3-LED combination (850, 970, 1050 nm); 0.99% for optimum 4-LED combination (850, 950, 970, 1020 nm) and 0.80% for the optimum 5-LED combination (665, 850, 950, 1020, 1050 nm).

Figure 18A:
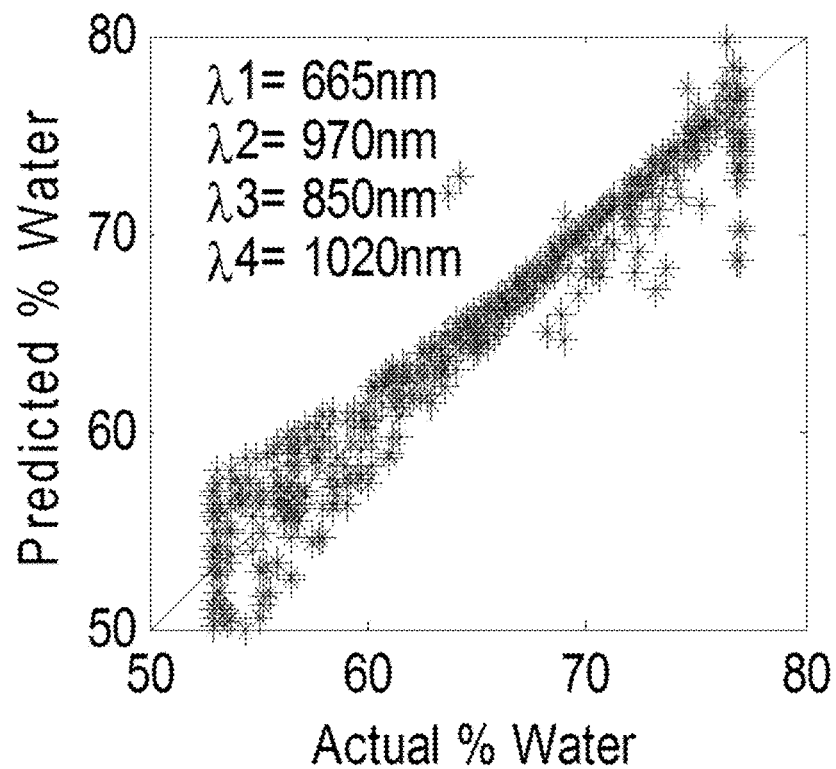
FIG. 18A illustrates tissue water content predicted by linear regression, using the equation % W=6.13 OD$\lambda_1$+309 OD $\lambda_2$−119 OD$\lambda_3$−166 OD$\lambda_4$, for an optimal combination of four LED sources, for example having a 665 nm LED.
Figure 18B:
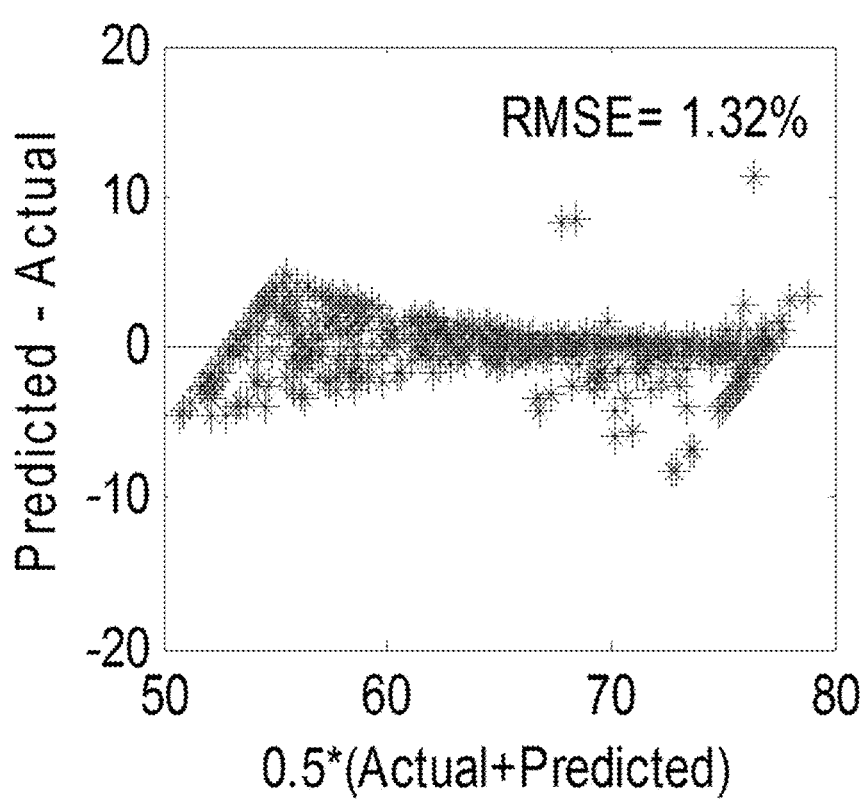
FIG. 18B illustrates the difference between predicted and actual % water from FIG. 18A.
Figure 19A:
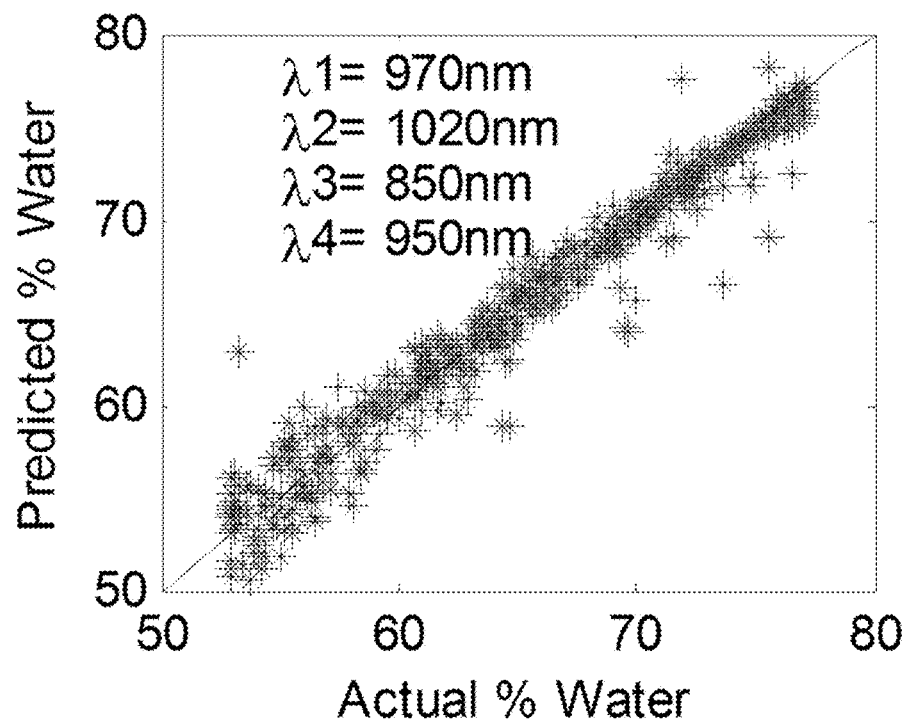
FIG. 19A illustrates tissue water content predicted by linear regression, using the equation % W=107 OD$\lambda_1$−183 OD$\lambda_2$−258 OD$\lambda_3$+328 OD$\lambda_4$, for an optimal combination of four LED sources.
Figure 19B:
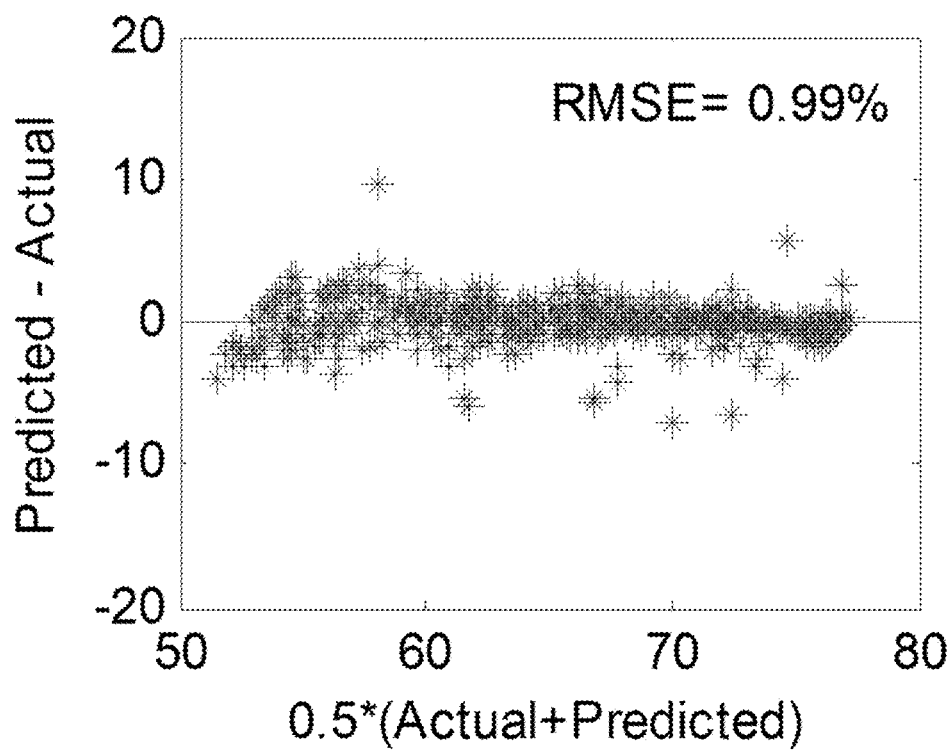
FIG. 19B illustrates the difference between predicted and actual % water from FIG. 19A.
Figure 20A:
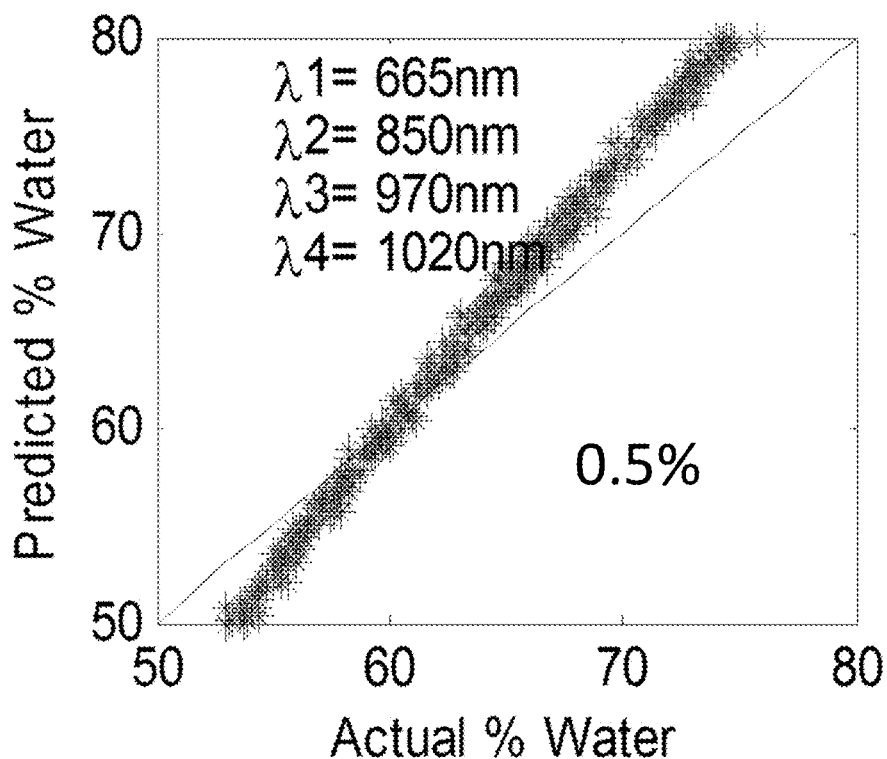
FIG. 20A illustrates predicted versus actual percentage of tissue water at 0.5% blood volume for the 4-LED combination in FIG. 18.
Figure 20B:
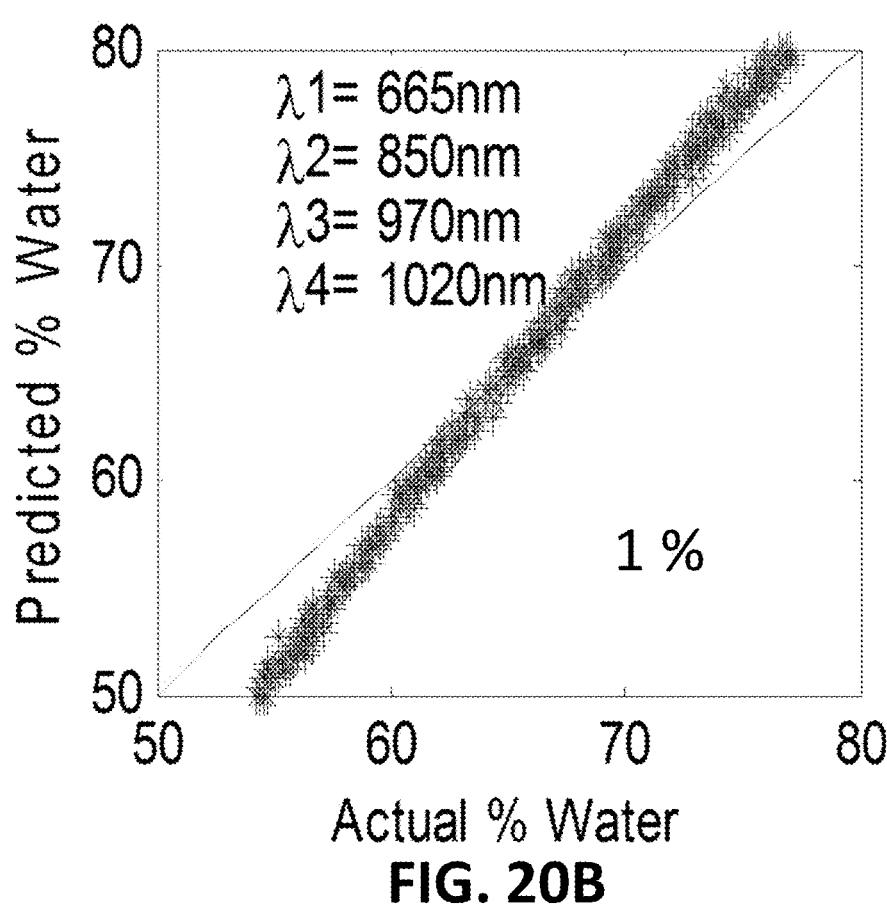
FIG. 20B illustrates predicted versus actual percentage of tissue water at 1% blood volume for the 4-LED combination in FIG. 18.
Figure 20C:
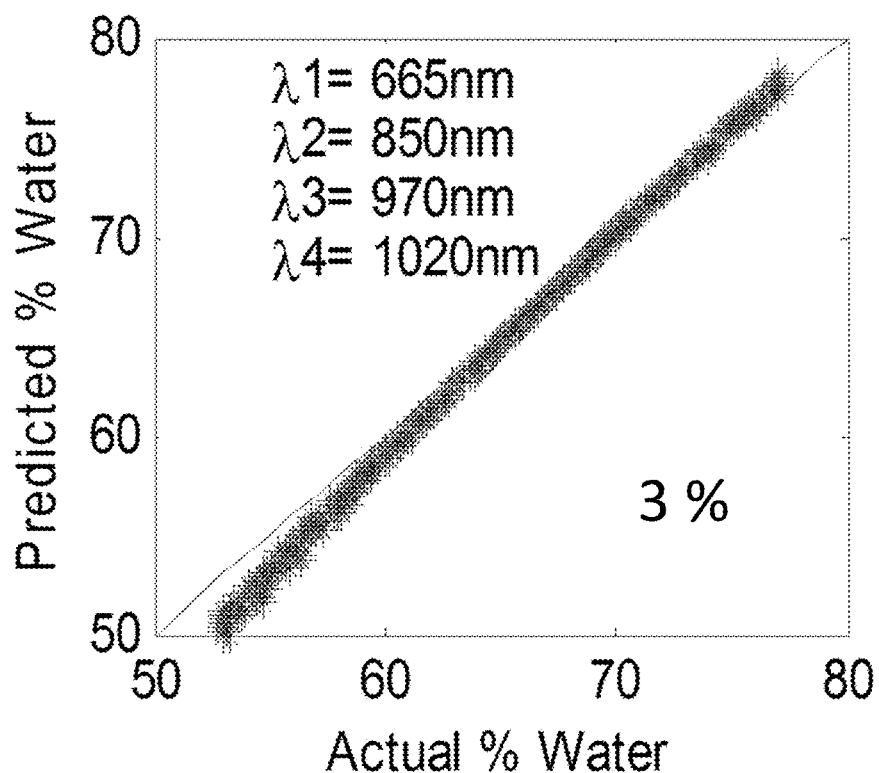
FIG. 20C illustrates predicted versus actual percentage of tissue water at 3% blood volume for the 4-LED combination in FIG. 18.
Figure 20D:
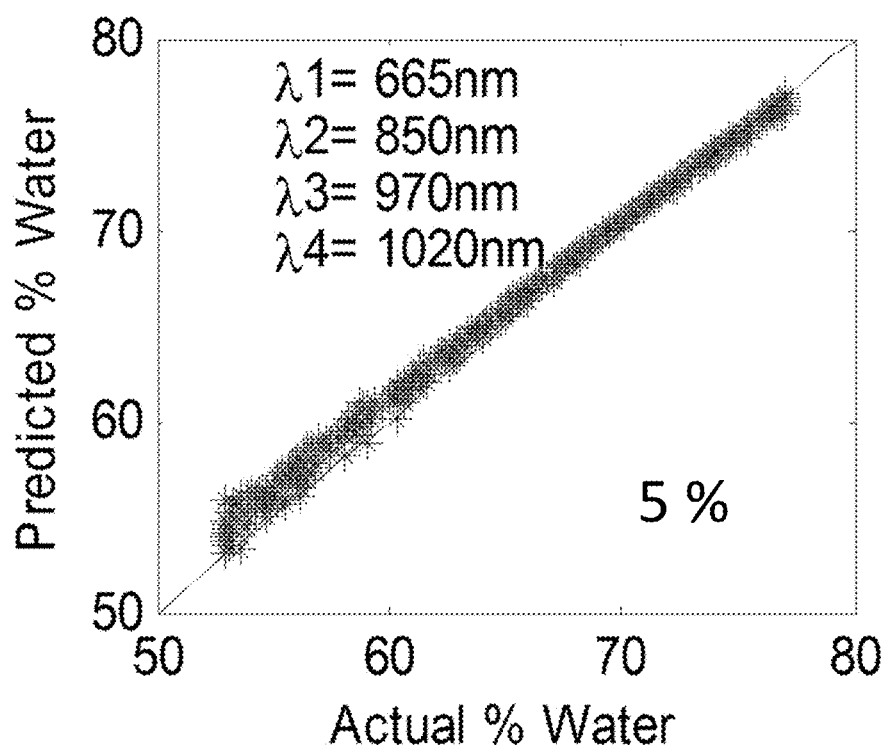
FIG. 20D illustrates predicted versus actual percentage of tissue water at 5% blood volume for the 4-LED combination in FIG. 18.
Figure 20E:
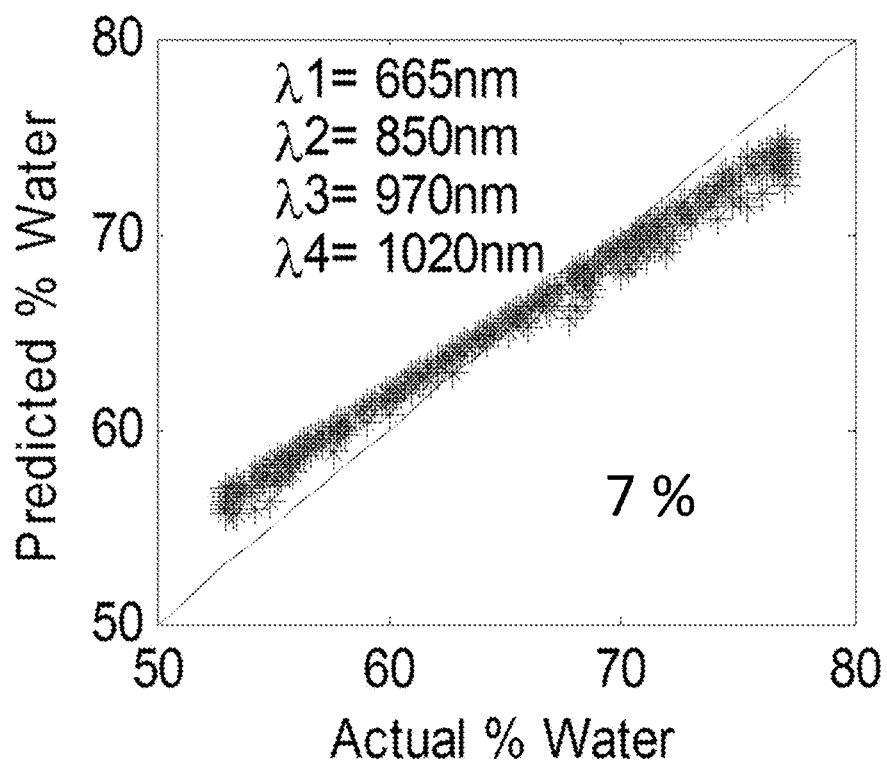
FIG. 20E illustrates predicted versus actual percentage of tissue water at 7% blood volume for the 4-LED combination in FIG. 18.
Figure 20F:
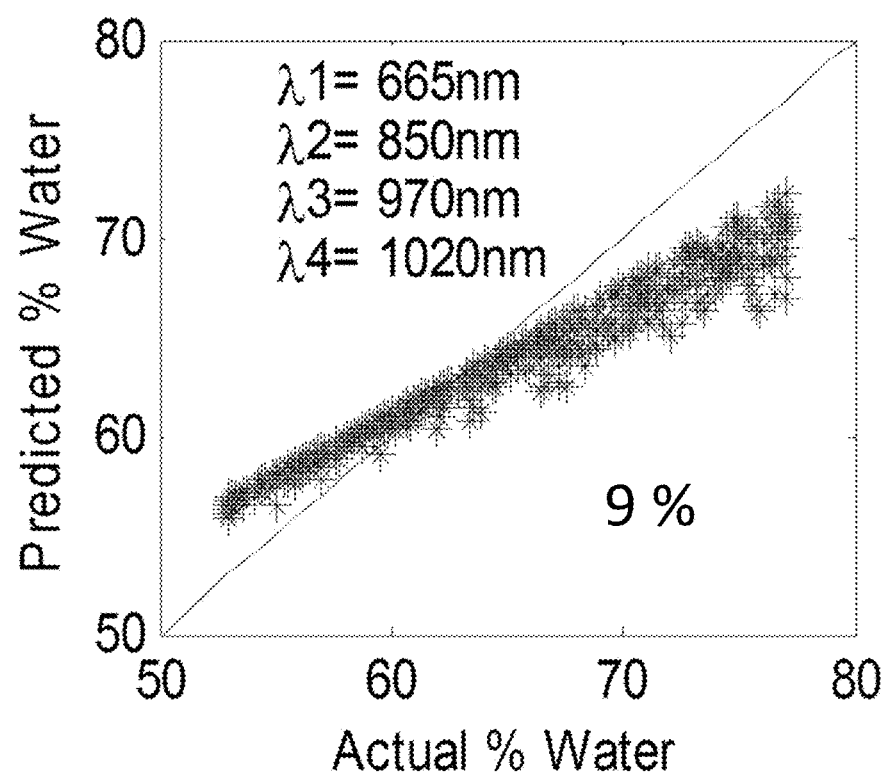
FIG. 20F illustrates predicted versus actual percentage of tissue water at 9% blood volume for the 4-LED combination in FIG. 18.
Figure 20G:
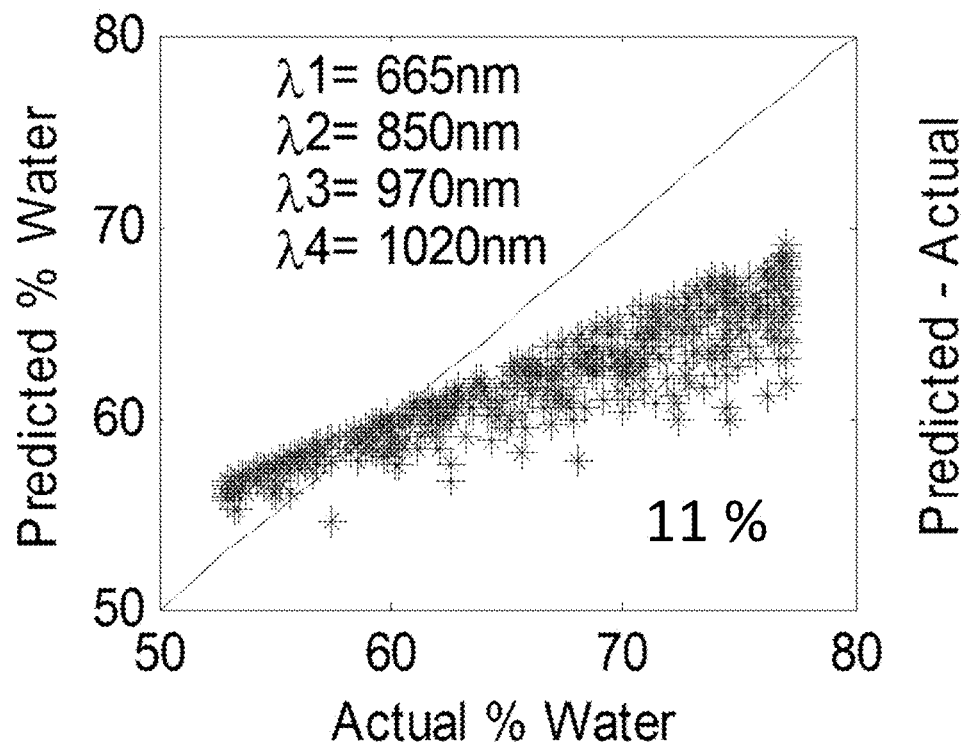
FIG. 20G illustrates predicted versus actual percentage of tissue water at 11% blood volume for the 4-LED combination in FIG. 18.
Figure 20H:
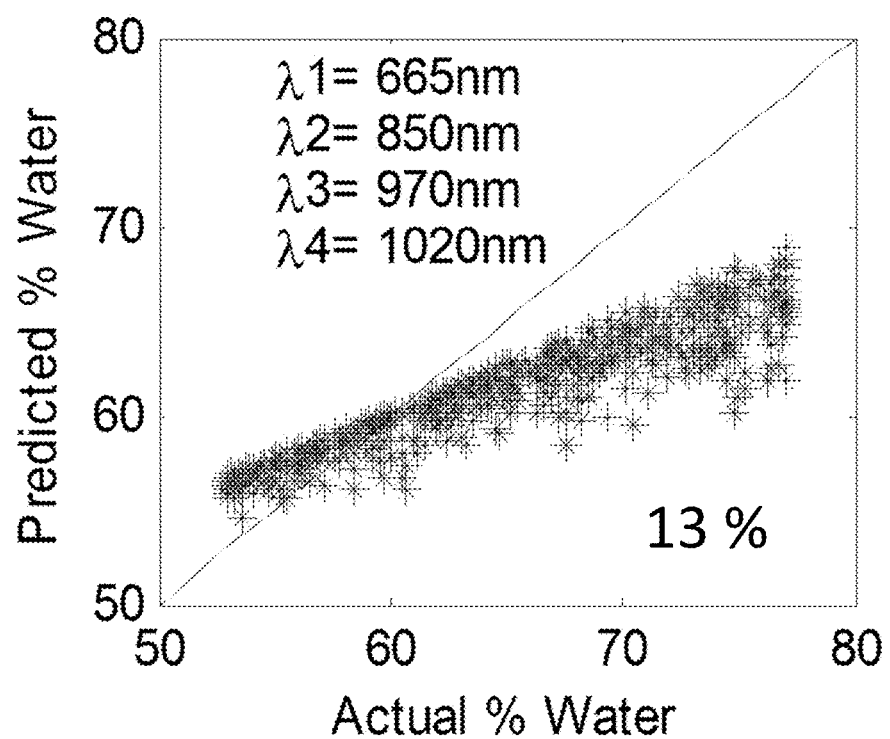
FIG. 20H illustrates predicted versus actual percentage of tissue water at 13% blood volume for the 4-LED combination in FIG. 18.
Figure 20I:
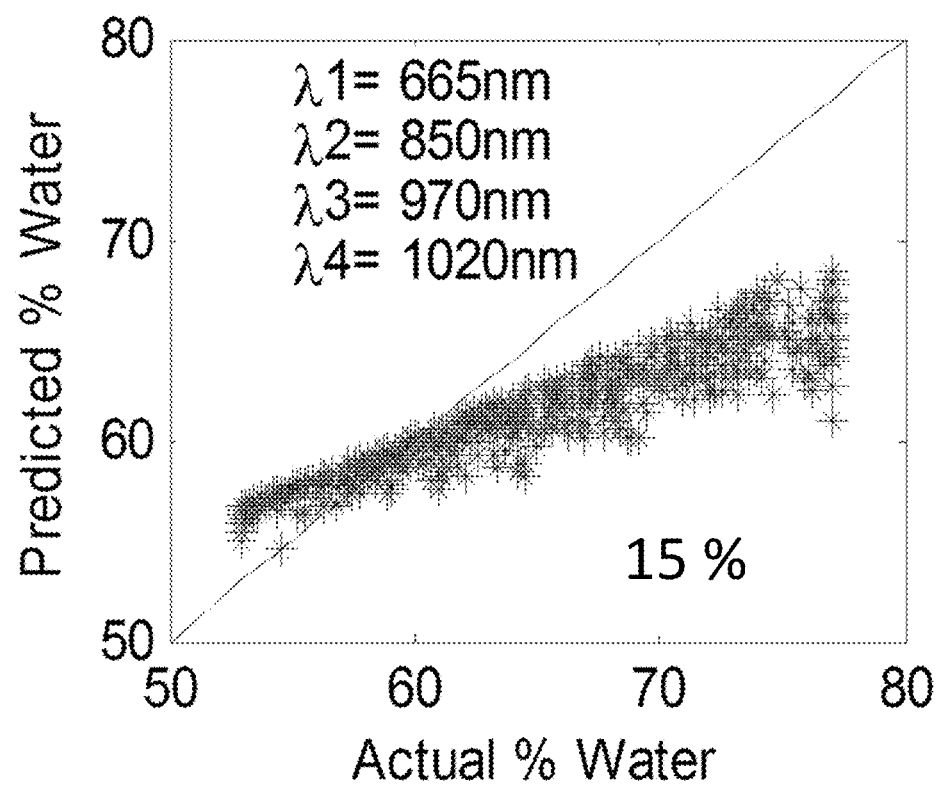
FIG. 20I illustrates predicted versus actual percentage of tissue water at 15% blood volume for the 4-LED combination in FIG. 18.

The 4-LED combinations tended to exclude the 665 nm LED, but the degradation in prediction error that resulted from including 665 nm was not large: 1.32% for optimum 4-LED combination (665, 850, 970, 1020 nm). FIGS. 18 and 19 compare the optimal 4-LED regression results for the cases with and without the 665 nm LED included.

FIG. 18 illustrates tissue water content predicted by linear regression, using the equation at the bottom of the figure, for an optimal combination of four LED sources with 665 nm LED included. For these simulations, the mean blood volume in the tissue was assumed to equal 5%, with a standard deviation of +/−2%. Thin, collimated source and detector beams were assumed, with a source-detector spacing of 14 mm.

FIG. 19 illustrates tissue water content predicted by linear regression, using the equation at the bottom of the figure for an optimal combination of four LED sources. For these simulations, the mean blood volume in the tissue was assumed to equal 5%, with a standard deviation of +/−2%. Thin, collimated source and detector beams were assumed, with a source-detector spacing of 14 mm.

RMS prediction error that can be expected using a linear OD algorithm based on 4 or 5 LED wavelengths is on the order of 1%. The residual error results mainly from the inability of the algorithm to correct completely for spectral baseline shifts and tilts caused by the wide variation of the volume of blood in the tissue. This effect can be seen more clearly from the plots in FIG. 20, which shows the relationship between the actual and predicted tissue water percentage for fixed background blood volume. For blood volumes below about 5%, actual water content can be predicted quite accurately at a fixed blood volume, provided that the blood volume is known.

Knowledge of the percent blood volume at a given site on a given subject would be a valuable input into the water prediction algorithm. If a good estimate of the percent blood volume could be obtained, the coefficients of the prediction equation could be then adjusted to suppress small changes in blood volume more effectively. FIG. 20 shows an example of the dependence of the coefficients of the 4-$\lambda$, prediction equation on blood volume.

The few methods for estimating blood volume and incorporating these estimates into the algorithms for measuring tissue water include: 1) use a separate multi-wavelength algorithm to measure absolute percent blood volume. Then adjust the water prediction coefficients according to model-derived equations, 2) as part of a calibration procedure, ask the user to induce a perturbation in blood volume through a prescribed sequence of movements (for example, arm lifts). Then, adjust the blood-volume-dependent component of the coefficients of the water prediction equation to minimize the change in the percentage water measurements during the perturbation period, 3) assign a target absolute percentage of tissue water for a particular site (for example, 68% for the forearm). Then, as part of a calibration procedure, adjust the blood-volume-dependent component of the coefficients of the water prediction equation iteratively until the measured percent water equals the target percent water or 4) dynamically adjust the blood-volume-dependent component of the coefficients of the water prediction equation to minimize the rapid changes in the percent water measurements, which are assumed to result from blood volume variations.

FIG. 20 illustrates predicted versus actual % tissue water at different blood volumes for the 4-LED combination in FIG. 18.

Figure 21:
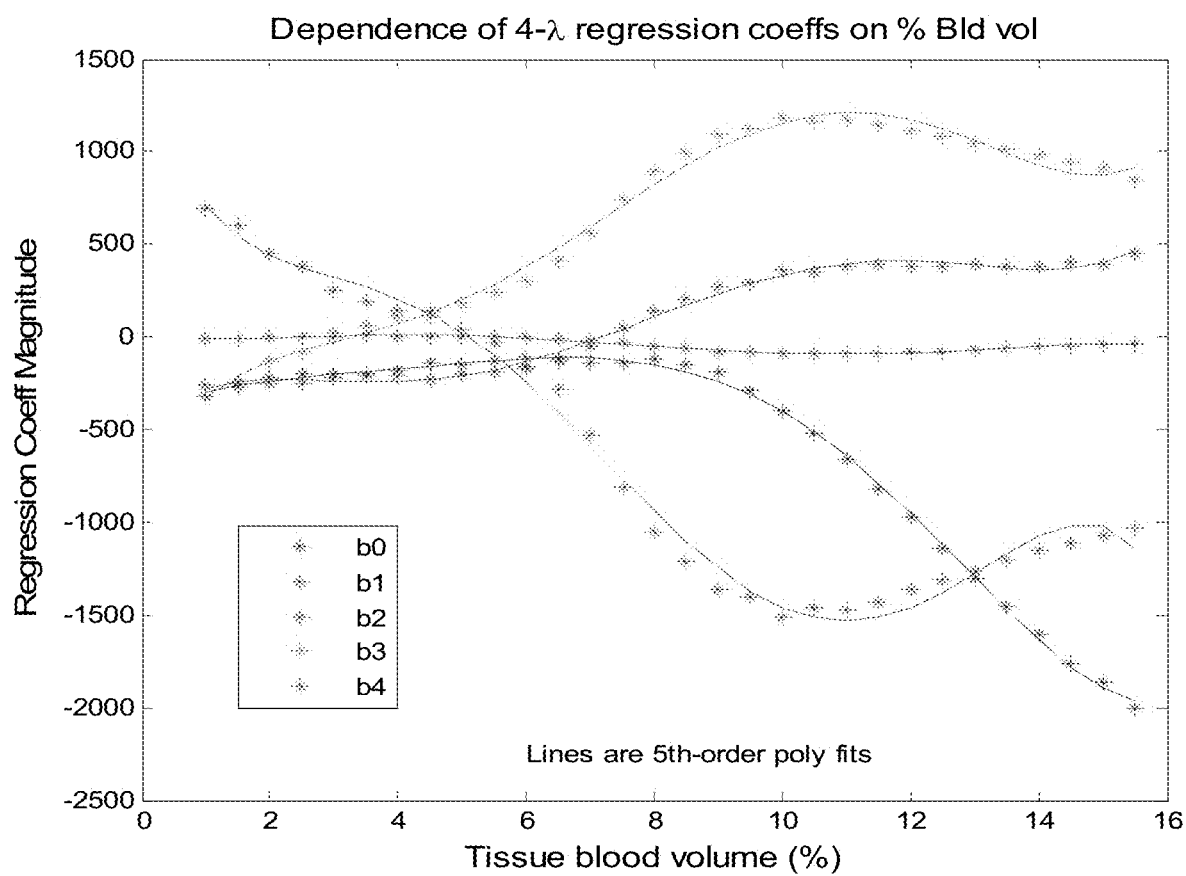
FIG. 21 illustrates the modeled effect of percent blood volume on the optimal coefficients of the 4-LED λ prediction equation $W = b_0 + b_1 OD_{665\ nm} + b_2 OD_{850\ nm} + b_3 OD_{970\ nm} + b_4 OD_{1020\ nm}$.
Figure 22A:
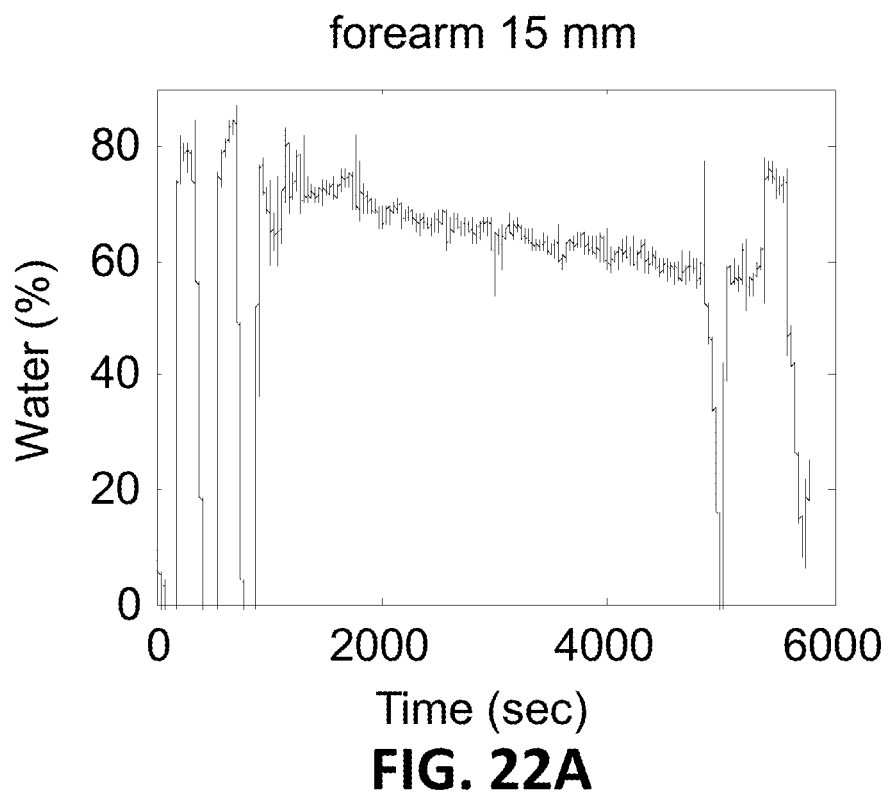
FIG. 22A shows the time course of the predicted water changes on a subject from the forearm at 15 mm, where % $W = 60.7 \ (OD_{665} - 2.75) - 656.4 \ (OD_{810} - 2.75) + 405.5 \ (OD_{850} - 2.75) - 171 \ (OD_{950} - 2.75)$.
Figure 22B:
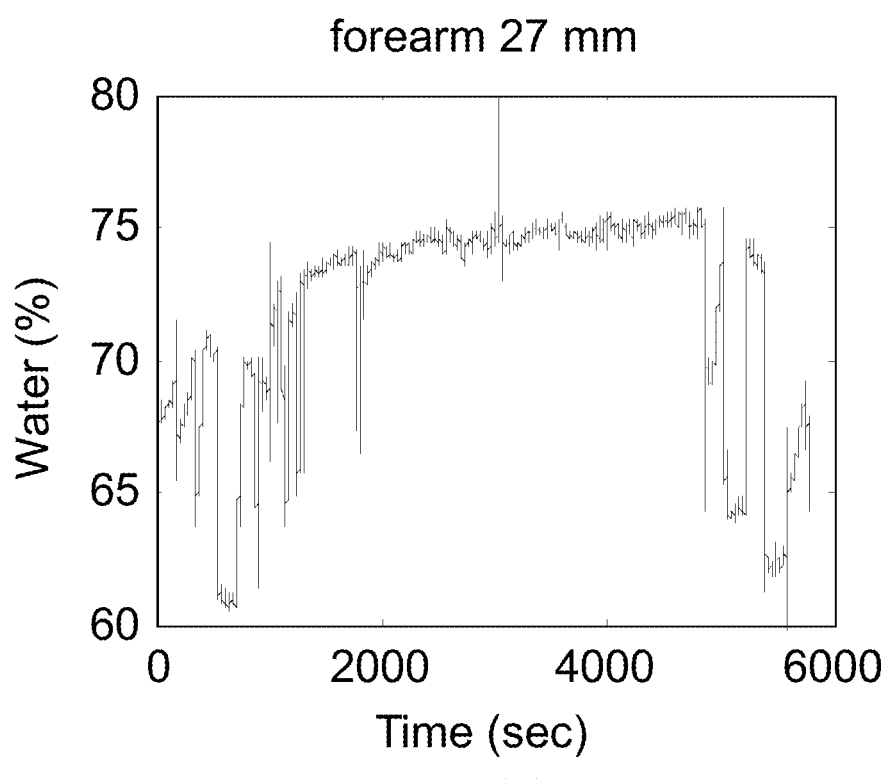
FIG. 22B shows the time course of the predicted water changes on a subject from the forearm at 27 mm, where % $W = 1.7 \ (OD_{665} - 4.6) + 44.9 \ (OD_{810} - 4.6) - 250.2 \ (OD_{850} - 4.6) + 239.6 \ (OD_{950} - 4.6)$.
Figure 22C:
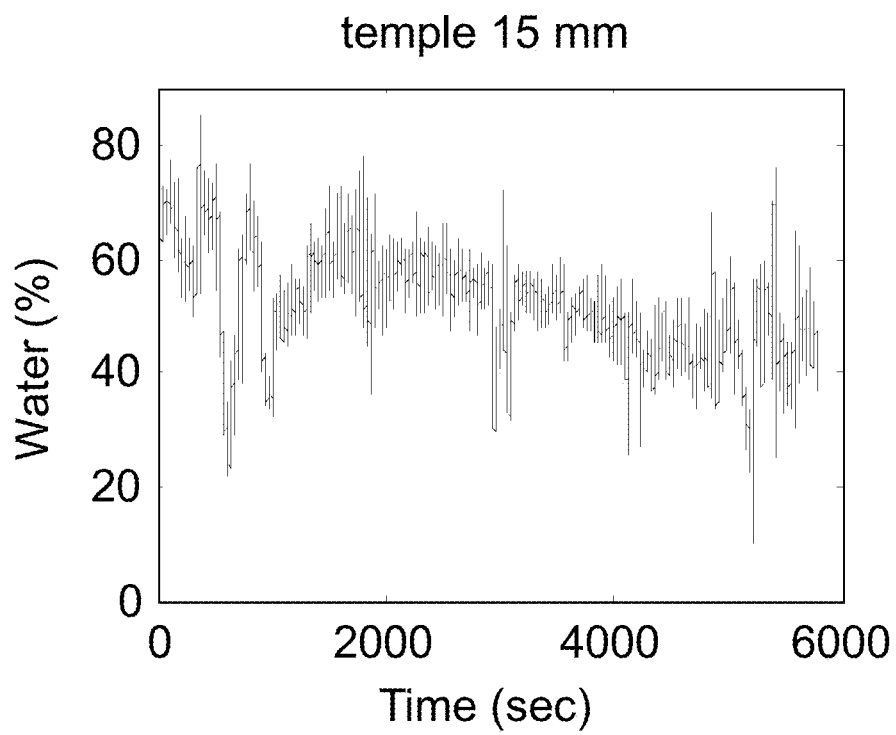
FIG. 22C shows the time course of the predicted water changes on a subject from the temple at 15 mm, where % $W = 60.7 \ (OD_{665} - 2.75) - 656.4 \ (OD_{810} - 2.75) + 405.5 \ (OD_{850} - 2.75) - 171 \ (OD_{950} - 2.75)$.
Figure 22D:
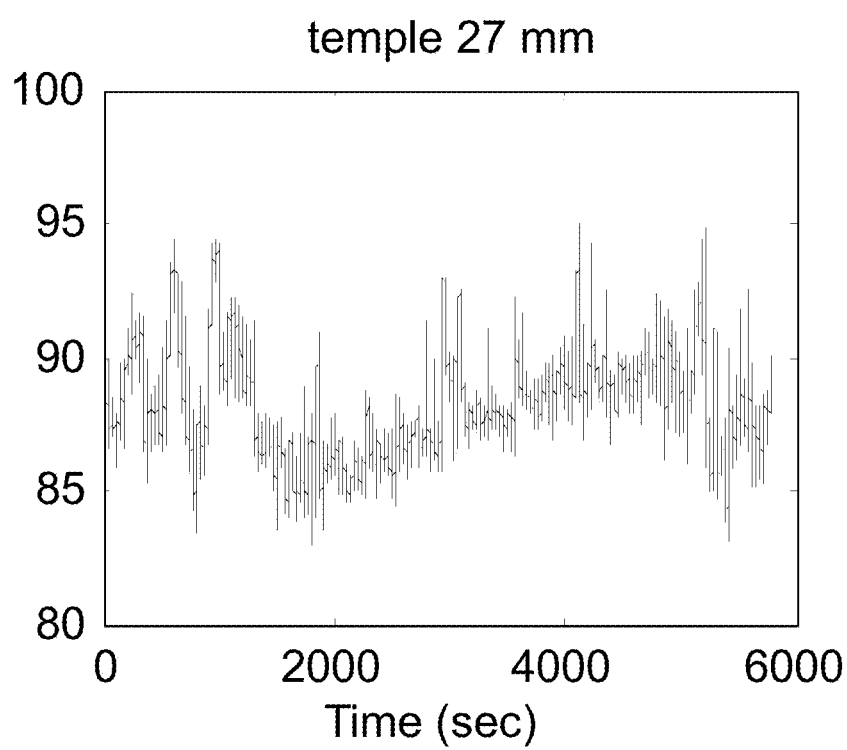
FIG. 22D shows the time course of the predicted water changes on a subject from the temple at 27 mm, where % $W = 1.7 \ (OD_{665} - 4.6) + 44.9 \ (OD_{810} - 4.6) - 250.2 \ (OD_{850} - 4.6) + 239.6 \ (OD_{950} - 4.6)$.
Figure 23A:
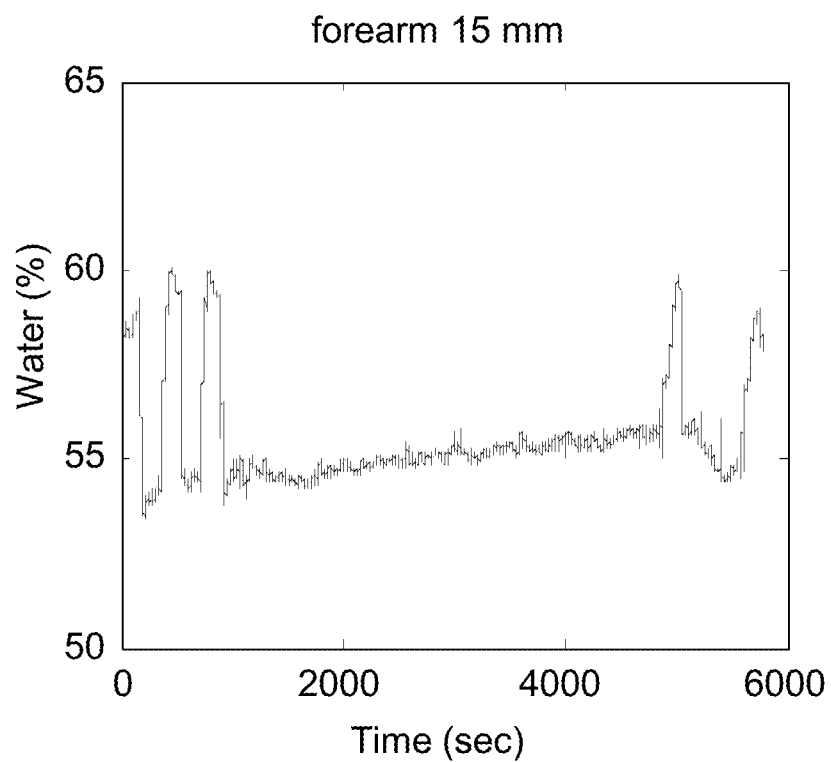
FIG. 23A illustrates time course of tissue water changes on a subject from the forearm at 15 mm, calculated by applying the theoretical regression equations, normalized by the mean of the optical densities (ODs) at all wavelengths at the time of rehydration (as illustrated, t=1080 s). % $W = (-4.4\ OD_{665} - 162.5 * OD_{810} + 191.9\ OD_{850} + 34.6\ OD_{950})/\text{mean}\ (OD_{665} + OD_{810} + OD_{850}\ OD_{950})_{@t=1000s}$.
Figure 23B:
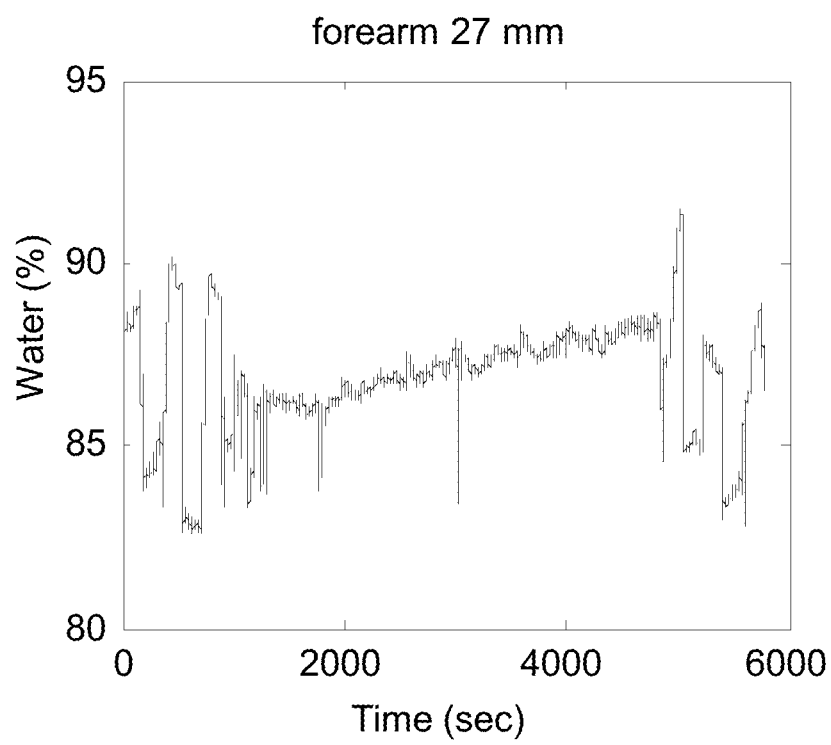
FIG. 23B illustrates time course of tissue water changes on a subject from the forearm at 27 mm, calculated by applying the theoretical regression equations, normalized by the mean of the optical densities (ODs) at all wavelengths at the time of rehydration (as illustrated, t=1080 s). % $W = (-5.4\ OD_{665} - 113.2 * OD_{810} + 138.0\ OD_{850} + 40.7\ OD_{950})/\text{mean}\ (OD_{665} + OD_{810} + OD_{850}\ OD_{950})_{@t=1000s}$.
Figure 23C:
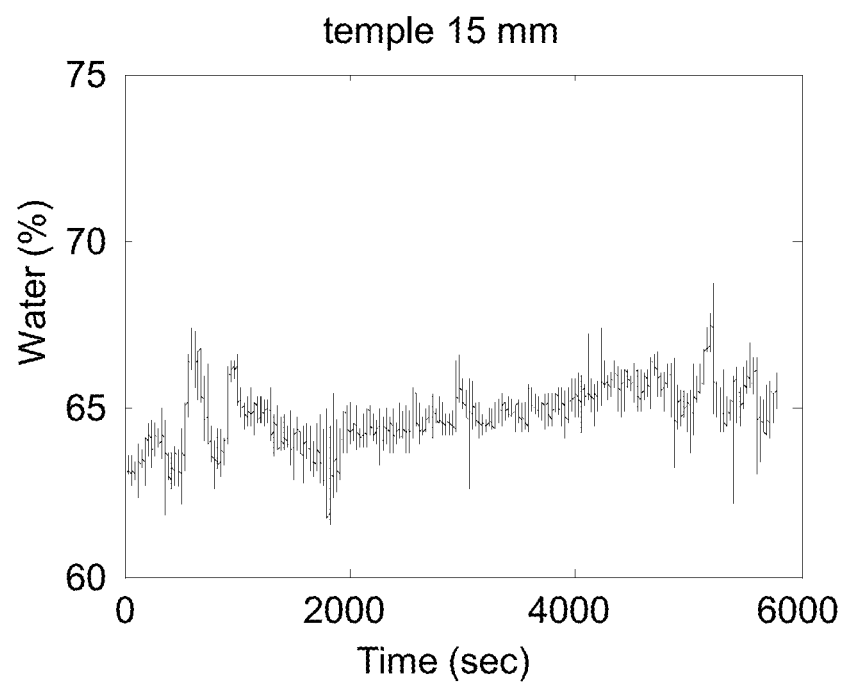
FIG. 23C illustrates time course of tissue water changes on a subject from the temple at 15 mm, calculated by applying the theoretical regression equations, normalized by the mean of the optical densities (ODs) at all wavelengths at the time of rehydration (as illustrated, t=1080 s). % $W = (-4.4\ OD_{665} - 162.5 * OD_{810} + 191.9\ OD_{850} + 34.6\ OD_{950})/\text{mean}\ (OD_{665} + OD_{810} + OD_{850}\ OD_{950})_{@t=1000s}$.
Figure 23D:
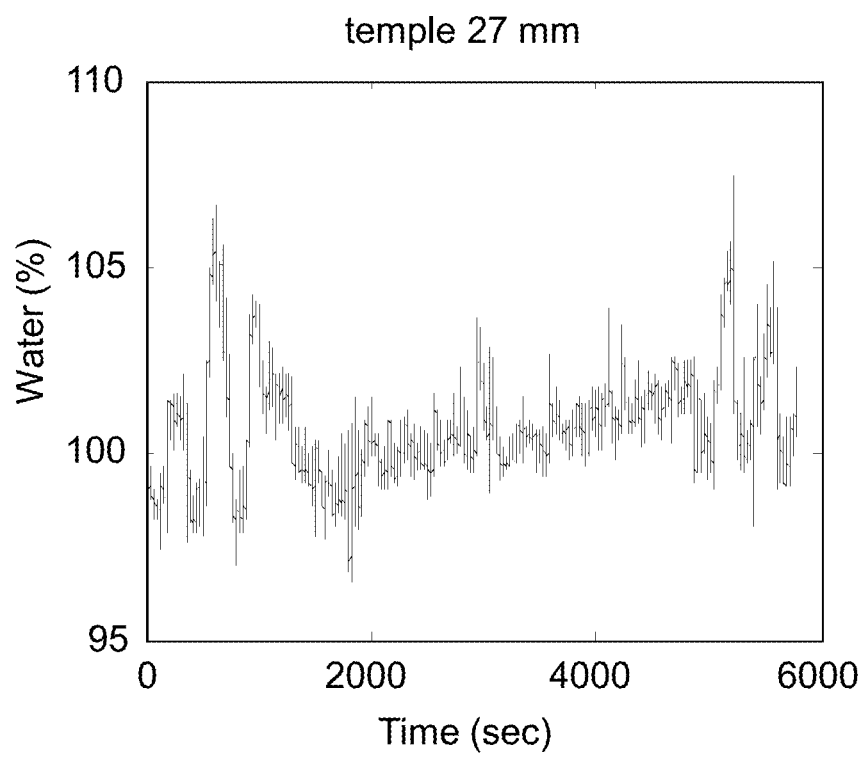
FIG. 23D illustrates time course of tissue water changes on a subject from the temple at 27 mm, calculated by applying the theoretical regression equations, normalized by the mean of the optical densities (ODs) at all wavelengths at the time of rehydration (as illustrated, t=1080 s). % $W = (-5.4\ OD_{665} - 113.2 * OD_{810} + 138.0\ OD_{850} + 40.7\ OD_{950})/\text{mean}\ (OD_{665} + OD_{810} + OD_{850}\ OD_{950})_{@t=1000s}$.

FIG. 21 illustrates modeled effect of percent blood volume on the optimal coefficients of the 4-LED $\lambda$ prediction equation.

The best-fit regression equations from the theoretical simulations were applied to data collected with the legacy sensor (665, 810, 850, and 970 nm) from a single subject. Although the exact time course of the tissue water changes that occurred during the experiment is not known, the correspondence between the percent water calculated from the theoretical regression equations and the expected trend based on weight changes was examined.

FIG. 22 shows the time course of the predicted water changes from the two measurement sites, the forearm and the temple. The periods before t=1000 s and after t=5000 s correspond to a series of standing and sitting exercises that were performed to induce blood volume variations. Rehydration began at t=1080 s.

The forearm and temple sites with 27 mm source-detector spacing showed tissue water changes with the expected positive trend direction and magnitude ($\Delta$=2 to 4%) over most of the rehydration period. However, the large changes in the percent water estimates during the stand/sit movements before and after the rehydration period suggest that the effect of blood volume changes still had a major influence of the water estimates. Data from both sites at the 15 mm source-detector spacing trended in the opposite direction, with unrealistically large changes in percent water ($\Delta$=−15 to −20%). Large differences between the effective blood volumes and/or scattering coefficients at the two different source-detector spacings induced a change in the slope of the actual-vs-predicted water regression curve (as in FIG. 20 example). The magnitude of these changes exceeded the ability of the model-based 4-wavelength expression to compensate.

FIG. 23 shows the time course of the predicted water changes for the regression equations normalized by the mean optical density at all wavelengths. The OD normalization had a substantial effect on the calculated tissue water trends: both the trend directions and magnitudes correspond better to expectation. However, the magnitude of the calculated tissue water changes induced by stand/sit exercises are still large relative to the slow upward trend observed during the rehydration period. Based on these observations from a single subject, Better results are expected for the new sensor configuration that includes additional LED wavelengths on both edges of the 970 nm water absorption band.

FIG. 22 illustrates time course of tissue water changes calculated by applying the theoretical regression equations to the measured OD values at 665, 810, 850, and 950 nm LED wavelength bands.

FIG. 23 illustrates time course of tissue water changes calculated by applying the theoretical regression equations, normalized by the mean of the ODs at all wavelengths at the time of rehydration (t=1080 s).

What is claimed is:

1. A wearable device for hydration monitoring comprising:
    an emitting component operable to emit light having at least three different wavelengths, wherein at least one of the wavelengths is in the range from 900 nm to 1600 nm for optical detection of a level of water;
    a sensor operable to receive a reflected portion of the emitted light;
    a processor operable to receive signals from the sensor; and
    a recessed cavity operable to avoid excess pressure on a user's skin;
    at least one breathing channel to aerate a space between the sensor and the skin, wherein the breathing channel comprises at least one of a capillary tube, an air channel with optical baffling, and/or micro-holes; and
    a layered material configured to be between the skin and the sensor capable of wicking moisture away from the sensor.

2. The wearable device of claim 1, wherein the layered material comprises a first layer comprising a breathable polymer and a second layer comprising a wicking material.

3. The wearable device of claim 1, wherein the layered material comprises a first layer comprising an adhesive, a second layer comprising a wicking material, and a third layer comprising a water-absorbing material.

4. The wearable device of claim 1, wherein the processor is operable to receive signals from the sensor and to calculate a vector projection selected for hydration monitoring.

5. The wearable device of claim 1, wherein the processor is operable to receive signals from the sensor and to calculate a regression to determine at least one of a blood volume level and/or a hydration level.

6. The wearable device of claim 1, wherein the sensor is a photodetector operable to receive a reflected portion of the emitted light, wherein at least three distances between the light emitting component and the photodetector are known, and the at least three distances allow monitoring of at least two different tissue beds with at least two different tissue depths.

7. The wearable device of claim 6, wherein the at least three distances are 8 mm, 14 mm, and 22 mm.

8. The wearable device of claim 1, wherein the device is operable to control pressure to regulate a hydration level of the skin underneath the sensor.

9. A method for hydration monitoring, the method comprising:
    emitting light from a light emitting component operable to emit light having at least three different wavelengths, wherein at least one of the wavelengths is in the range from 900 nm to 1600 nm for optical detection of a level of water;
    detecting light with at least one photodetector, wherein at least three distances between the light emitting component and the photodetector are known, and the at least three distances allow monitoring of at least two different tissue beds with at least two different tissue depths;
    aerating, via at least one breathing channel, a space formed between the at least one photodetector and a skin of a user;
    wicking, via a layered material configured to be between the skin and the photodetector, moisture away from the photodetector.

10. The method of claim 9, further comprising calculating a vector projection selected for hydration monitoring.

11. The method of claim 9, further comprising calculating a regression to determine at least one of a blood volume level and/or a hydration level.

12. The method of claim 11, wherein the regression is a linear regression.

13. The method of claim 9, further comprising detecting a slowly-varying analyte, wherein the slowly-varying analyte is one or more of collagen, lipid, cytochrome oxidase, melanin, or total hemoglobin.

14. The method of claim 13, further comprising adapting a weighting of the wavelengths dynamically to remove interference that varies over a time interval shorter than that of the slowly varying analyte.

15. The method of claim 9, wherein the at least two different tissue beds comprise one tissue bed that is a shallow tissue bed and another tissue bed that is a deep tissue bed.

16. The method of claim 15, wherein the shallow tissue bed is selected from the group consisting of an epidermis, and bone and the deep tissue bed is selected from the group consisting of a muscle, a lipid, a subarachnoid space, or gray matter.

17. The method of claim 9, further comprising calculating the ratio of signals from the at least two different tissue beds.

18. The method of claim 9, wherein one of the at least two different tissue depths is used as a reference.

19. The method of claim 9, further comprising canceling out at least one other physiological change selected from at least one of blood volume, oxygenation, motion, or pressure change.

* * * * *